(12) United States Patent
Murata et al.

(10) Patent No.: US 11,207,506 B2
(45) Date of Patent: Dec. 28, 2021

(54) BALLOON CATHETER, METHOD OF MANUFACTURING A BALLOON CATHETER, AND TREATMENT METHOD

(71) Applicant: TERUMO KABUSHIKI KAISHA, Tokyo (JP)

(72) Inventors: Yu Murata, Kanagawa (JP); Hiroshi Goto, Kanagawa (JP); Ryosuke Suzuki, Kanagawa (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 233 days.

(21) Appl. No.: 16/127,427

(22) Filed: Sep. 11, 2018

(65) Prior Publication Data

US 2019/0009064 A1   Jan. 10, 2019

Related U.S. Application Data

(63) Continuation of application No. PCT/JP2017/011634, filed on Mar. 23, 2017.

(30) Foreign Application Priority Data

Mar. 23, 2016   (JP) .............................. JP2016-058040

(51) Int. Cl.
   *A61M 25/10*   (2013.01)
   *A61L 29/16*   (2006.01)
   (Continued)

(52) U.S. Cl.
   CPC ....... *A61M 25/1029* (2013.01); *A61K 31/337* (2013.01); *A61K 31/436* (2013.01);
   (Continued)

(58) Field of Classification Search
   CPC .... A61M 2025/105; A61M 2025/1086; A61M 2025/1075; A61M 2025/1004;
   (Continued)

(56) References Cited

U.S. PATENT DOCUMENTS 8,114,049 B2 * 2/2012 Freyman ................. A61L 29/16
                                               604/103.08
9,730,726 B2 * 8/2017 Bacino .............. A61M 25/1002
(Continued)

FOREIGN PATENT DOCUMENTS

EP      3 106 197 A1    12/2016
JP     2012-533338 A    12/2012
(Continued)

OTHER PUBLICATIONS

International Search Report (PCT/ISA/210) dated Jun. 20, 2017, by the Japanese Patent Office as the International Searching Authority for International Application No. PCT/JP2017/011634.
(Continued)

*Primary Examiner* — Laura A Bouchelle
*Assistant Examiner* — Anna E Goldberg-Richmeier
(74) *Attorney, Agent, or Firm* — Buchanan Ingersoll & Rooney PC

(57) ABSTRACT

A balloon catheter is disclosed capable of effectively delivering a drug to living body tissue and a manufacturing method of the balloon catheter, and a treatment method. The balloon catheter has a balloon at a distal portion of a catheter shaft, and is provided on a surface of the balloon with elongate bodies which are crystals of a water-insoluble drug extending in a longitudinal direction. The surface of the balloon is provided with crystal conjugates formed of a plurality of elongate bodies united to one another while being in a tilted state.

18 Claims, 15 Drawing Sheets

(51) Int. Cl.
*A61K 31/436* (2006.01)
*A61K 31/337* (2006.01)

(52) U.S. Cl.
CPC ............. *A61L 29/16* (2013.01); *A61M 25/10* (2013.01); *A61L 2300/416* (2013.01); *A61L 2300/63* (2013.01); *A61M 2025/105* (2013.01); *A61M 2025/1031* (2013.01)

(58) Field of Classification Search
CPC .. A61M 2025/1081; A61M 2025/1031; A61M 2025/0057; A61M 25/104; A61M 25/0045; A61L 2300/60; A61L 2300/63; A61L 2300/416
See application file for complete search history.

(56) References Cited

U.S. PATENT DOCUMENTS

| | | | |
|---|---|---|---|
| 2009/0246252 A1* | 10/2009 | Arps | A61L 29/145 424/425 |
| 2011/0015664 A1 | 1/2011 | Kangas et al. | |
| 2011/0054396 A1* | 3/2011 | Kangas | A61L 29/16 604/103.02 |
| 2014/0271775 A1* | 9/2014 | Cleek | A61L 27/56 424/423 |
| 2016/0008522 A1 | 1/2016 | Yamashita et al. | |
| 2016/0038648 A1* | 2/2016 | Gemborys | A61L 27/54 424/423 |

FOREIGN PATENT DOCUMENTS

| | | |
|---|---|---|
| JP | 2013-502984 A | 1/2013 |
| JP | 2015-042280 A | 3/2015 |
| WO | 2014/163092 A1 | 10/2014 |
| WO | 2015/151876 A1 | 10/2015 |
| WO | 2015/174000 A1 | 11/2015 |

OTHER PUBLICATIONS

Written Opinion (PCT/ISA/237) dated Jun. 20, 2017, by the Japanese Patent Office as the International Searching Authority for International Application No. PCT/JP2017/011634.

The extended European Search Report dated Aug. 21, 2019, by the European Patent Office in corresponding European Patent Application No. 17770321.2-1109. (7 pages).

English translation of the Written Opinion of the International Searching Authority and International Search Report dated Jun. 20, 2017 in International Application No. PCT/JP2017/011634.

* cited by examiner

BALLOON CATHETER, METHOD OF MANUFACTURING A BALLOON CATHETER, AND TREATMENT METHOD

CROSS-REFERENCES TO RELATED APPLICATIONS

This application is a continuation of International Application No. PCT/JP2017/011634 filed on Mar. 23, 2017, which claims priority to Japanese Application No. 2016-058040 filed on Mar. 23, 2016, the entire contents of both of which is incorporated herein by reference.

TECHNICAL FIELD

The present disclosure generally relates to a balloon catheter having a balloon coated on its surface with a drug, a method of manufacturing a balloon catheter, and a treatment method.

BACKGROUND DISCUSSION

For improving lesion affected areas (stenosed parts) in body lumens, balloon catheters are widely used. A balloon catheter normally includes an elongate catheter shaft, and a balloon which is provided on the distal side of the catheter shaft and is inflatable in the radial direction. After the balloon in a deflated state is brought to a target site in the body by way of a thin body lumen, the balloon is inflated, whereby the lesion affected area can be pushed wide open (widened).

On the other hand, if a lesion affected area is forcibly pushed wide open by the balloon, excessive proliferation of endothelial cells may occur, causing new stenosis (restenosis) at the lesion affected area. In view of this, recently, drug eluting balloons (DEBs) in which a surface of a balloon is coated with a drug for restraining stenosis have been used. The drug eluting balloon, by being inflated, is able to release the drug contained in the coating on the surface of the balloon to the lesion affected area and transfer the drug into living body tissue, thereby restraining restenosis.

In recent years, it has been becoming clear that the morphological form of the drug in the coating on the balloon surface influences the releasing property of the drug from the balloon surface and/or the tissue transferability of the drug at the lesion affected area. For instance, U.S. Patent Application Publication No. 2014/0271775 describes a balloon catheter in which crystals of a drug are formed in elongate form on a surface of a balloon.

SUMMARY

For enhancing a therapeutic effect, a drug eluting balloon catheter is desirably configured in such a manner that the deliverability (i.e., transferability of the drug onto tissue) of the drug on the balloon surface to living body tissue is relatively high.

The present disclosure has been made for solving the above-mentioned problem. It is an object of the present disclosure to provide a balloon catheter by which a drug can be effectively delivered to living body tissue, a method of manufacturing a balloon catheter, and a treatment method.

A balloon catheter according to the present disclosure for achieving the aforesaid object is a balloon catheter having a balloon at a distal portion of a catheter shaft and provided on a surface of the balloon with elongate bodies which are crystals of a water-insoluble drug extending in a longitudinal direction, in which the surface of the balloon is provided with a crystal conjugate formed of the plurality of elongate bodies that are joined to one another while being in a tilted state.

In addition, a method of manufacturing a balloon catheter according to the present disclosure for achieving the aforesaid object is a method of manufacturing a balloon catheter provided on a surface of a balloon with elongate bodies which are crystals of a water-insoluble drug extending in a longitudinal direction, the method including: a step of forming the elongate bodies having mutually independent long axes on the surface of the balloon; a step of forming the balloon with a wing portion projecting in a radial direction; and a step of laying the wing portion, formed in the balloon, flat along a circumferential direction, in which in either the step of forming the balloon with the wing portion or the step of laying flat the wing portion of the balloon, the mutually independent elongate bodies on the surface of the balloon are united with the adjacent elongate bodies while tilting them by a force and heat applied for deforming the balloon, thereby to form a crystal conjugate in which the plurality of the elongate bodies overlap with each other at a position in the longitudinal direction and are united with one another.

In addition, a method of manufacturing a balloon catheter according to the present disclosure for achieving the aforesaid object is a method of manufacturing a balloon catheter provided on a surface of a balloon with elongate bodies which are crystals of a water-insoluble drug extending in a longitudinal direction, the method including: a step of forming on the surface of the balloon a crystal conjugate in which the plurality of the elongate bodies overlap with each other at a position in the longitudinal direction and are united with one another; a step of forming the balloon with a wing portion projecting in a radial direction; and a step of laying the wing portion, formed in the balloon, flat along a circumferential direction, in which in either the step of forming the balloon with the wing portion or the step of laying flat the wing portion of the balloon, the crystal conjugate is tilted relative to the surface of the balloon by a force and heat applied for deforming the balloon.

In addition, a treatment method according to the present disclosure for achieving the aforesaid object is a treatment method of delivering a drug to a lesion affected area in a body lumen by use of a balloon catheter, the treatment method including: a step of inserting the balloon into the body lumen to deliver the balloon to the lesion affected area; a step of inflating the balloon to press the elongate bodies against living body tissue; and a step of deflating the balloon and withdrawing the balloon out of the body lumen.

In the balloon catheter configured as aforesaid, at the time of inserting the balloon into a body lumen, separation of the elongate bodies from the surface of the balloon can be restrained. In addition, upon inflation of the balloon at a lesion affected area, the crystal conjugate is separated to be the elongate bodies in an independent state, and, therefore, transferability of the drug to living body tissue can be improved.

Where the elongate bodies in the tilted state which form the crystal conjugates are so disposed as to form angles of not more than 30 degrees relative to the surface of the balloon, it can be relatively ensured that the elongate bodies are hardly separated (or dissected) from the surface of the balloon at the time of inserting the balloon into the body lumen.

The crystal conjugate is formed of the plurality of elongate bodies that overlap with each other at a position in the longitudinal direction and are joined to and united (i.e., joined) with one another. Therefore, the shapes of the elongate bodies are left as they are in the crystal conjugate, which can help ensure that the crystal conjugate is easily separated upon inflation of the balloon, to take the form of the elongate bodies after separation, so that the drug can be effectively transferred to the living body tissue.

In accordance with an aspect, the crystal conjugate is cracked when the balloon is inflated. Therefore, when the surface of the balloon is pressed against living body tissue, the crystal conjugate is separated to take the form of the independent elongate bodies, so that the drug can be easily transferred to the living body tissue.

Where the water-insoluble drug is rapamycin, paclitaxel, docetaxel, or everolimus, restenosis at a stenosed part in a blood vessel can be favorably restrained (or prevented).

According to the method of manufacturing a balloon catheter configured as aforesaid, in either the step of forming the balloon with the wing portion or the step of laying flat the wing portion of the balloon, the crystal conjugate in a state in which the elongate bodies are tilted can be formed on the surface of the balloon, by utilizing the force and heat applied for deforming the balloon.

In addition, according to the method of manufacturing a balloon catheter configured as aforesaid, in either the step of forming the balloon with the wing portion or the step of laying flat the wing portion of the balloon, the elongate bodies constituting the crystal conjugate having been preliminarily formed on the surface of the balloon can be tilted, through utilization of the force and heat applied for deforming the balloon.

According to the treatment method configured as aforesaid, at the time of moving the balloon in the folded state within a blood vessel, it is possible, owing to the presence of the crystal conjugate, to restrain (or prevent) the drug from being lost (i.e., falling off or being removed from) during insertion of the balloon, and to effectively deliver the drug to the target position. When the balloon is inflated at a lesion affected area, the crystal conjugate comes to take the form of the elongate bodies, whereby the drug can be effectively transferred to the lesion affected area.

When the balloon is inflated, cracks are formed in the crystal conjugate on the balloon. Therefore, when the surface of the balloon is pressed against living body tissue, the crystal conjugate is separated to take the form of the independent elongate bodies, so that the drug can be easily transferred to the living body tissue.

DETAILED DESCRIPTION

Figure 1:
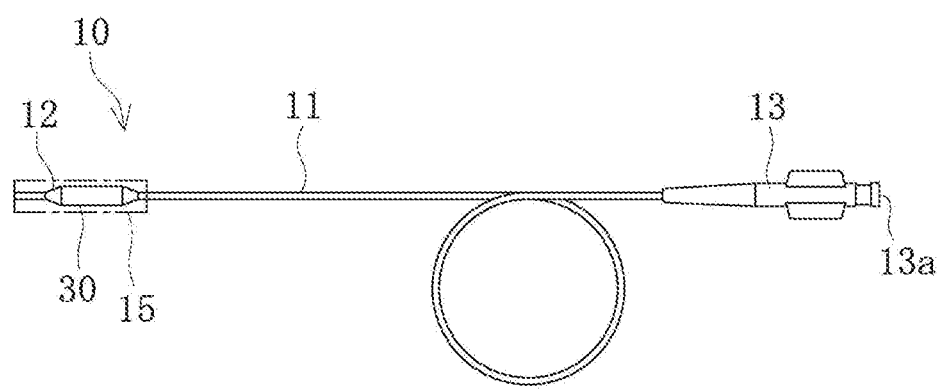
FIG. 1 is a front view of a balloon catheter according to the present embodiment.

An embodiment of the present disclosure will be described below referring to the drawings. The dimensional ratios in the drawings may be exaggerated and different from the actual ratios, for convenience of explanation. In addition, in the present specification, the side on which a balloon catheter 10 is inserted into a body lumen will be referred to as "distal end" or "distal side," while the operator's hand side on which the balloon catheter 10 is operated will be referred to as "proximal end" or "proximal side."

First, a balloon catheter of the present embodiment will be described. As depicted in FIG. 1, the balloon catheter 10 includes an elongate hollow catheter shaft 11, a balloon 12 provided at a distal-side end portion of the catheter shaft 11, a coating layer 30 which contains a drug and is provided on a surface of the balloon 12, and a hub 13 firmly attached to a proximal-side end portion of the catheter shaft 11. The balloon 12 provided with the coating layer 30 is protected by being covered with a protective sheath 15 until put to use.

The length in an axial direction of the balloon 12 is not particularly limited, and is, for example, preferably 5 mm to 500 mm, more preferably 10 mm to 300 mm, and still more preferably 20 mm to 200 mm.

The outside diameter of the balloon 12 when inflated is not specifically restricted, and is, for example, preferably 1 mm to 10 mm, and more preferably 2 mm to 8 mm.

The surface of the balloon 12 before the formation of the coating layer 30 is smooth and non-porous. The outer surface of the balloon 12 before the formation of the coating layer 30 may have minute (i.e., extremely small) holes that do not pierce through the film. Alternatively, the outer surface of the balloon 12 before the formation of the coating layer 30 may have both a region of being smooth and non-porous and a region of having minute holes that do not pierce through the film. The minute (i.e., extremely small) holes may be sized to have, for example, a diameter of 0.1 µm to 5 µm and a depth of 0.1 µm to 10 µm, and one or a plurality of holes may be provided per crystal. In addition, the minute holes may be sized to have, for example, a diameter of 5 µm to 500 µm and a depth of 0.1 µm to 50 µm, and one or a plurality of crystals may be provided per one hole.

This balloon catheter 10 is one such that the elongate catheter shaft 11 is inserted into a living body organ, and the balloon 12 provided on the distal side of the balloon 12 of the balloon catheter shaft 11 is inflated at a lesion affected area, whereby the lesion affected area can be pushed wide open (widened), thereby performing treatment.

Figure 2:
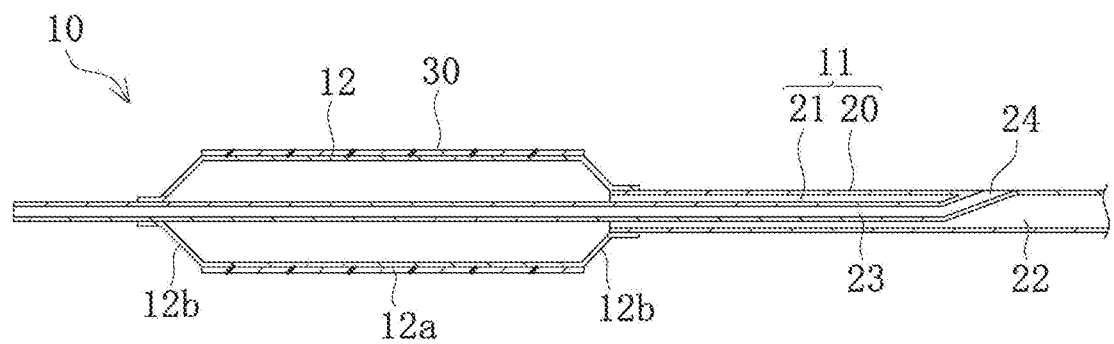
FIG. 2 is a sectional view of a distal portion of the balloon catheter.

Now, the structures of a distal portion of the catheter shaft 11 and the balloon 12 will be described below. As depicted in FIG. 2, the catheter shaft 11 includes a hollow outer tube 20, and an inner tube 21 which is a hollow inside support. The inner tube 21 is accommodated in the hollow inside of the outer tube 20, and the catheter shaft 11 has a double-tube structure at a distal portion of the catheter shaft 11. The hollow inside of the inner tube 21 forms a guide wire lumen 23 for passing a guide wire 14 therethrough. In addition, in the hollow inside of the outer tube 20 and on the outside of the inner tube 21, there is formed an inflation lumen 22 for passing therethrough an inflation fluid for the balloon 12. The inner tube 21 is opening to the exterior at an opening portion 24. The inner tube 21 protrudes to the distal side beyond a distal end of the outer tube 20.

Of the balloon 12, a proximal-side end portion is fixed (held or attached) to a distal portion of the outer tube 20, and a distal-side end portion is fixed to a distal portion of the inner tube 21. This results in that the inside of the balloon 12 communicates with the inflation lumen 22. With the inflation fluid injected through the inflation lumen 22 into the balloon 12, the balloon 12 can be inflated. The inflation fluid may be a gas or a liquid; for example, gases such as helium gas, $CO_2$ gas, $O_2$ gas, air, or mixed gas and liquids such as saline or a contrast agent, can be used as the inflation fluid. Note that in FIG. 2, the balloon 12 is in an inflated state.

At a central portion in regard of the axial direction of the balloon 12, there is formed a hollow cylindrical straight portion 12a (inflatable portion) having an equal outside diameter when inflated. Tapered portions 12b where the outside diameter gradually varies are formed on both sides of the straight portion 12a in regard of the axial direction. In addition, a coating layer 30 which contains a drug is formed on the whole part of the surface of the straight portion 12a. Note that the range of the balloon 12 in which the coating layer 30 is formed is not limited only to the straight portion 12a; the range may include at least part of the tapered portions 12b in addition to the straight portion 12a, or may be only part of the straight portion 12a.

The outer tube 20 and the inner tube 21 are preferably formed from a material which has a certain degree of flexibility. Examples of such a material include polyolefins such as polyethylene, polypropylene, polybutene, ethylene-propylene copolymers, ethylene-vinyl acetate copolymers, ionomers, or mixtures of two or more of the polyolefins, flexible polyvinyl chloride resin, polyamides, polyamide elastomers, polyesters, polyester elastomers, polyurethane, fluororesins such as polytetrafluorothylene, etc., silicone rubbers, and latex rubbers.

Preferably, the balloon 12 has a certain degree of flexibility and a certain degree of hardness such that the drug can be released from the coating layer 30 provided on the surface of the balloon 12 when the balloon 12 is inflated upon arrival at a blood vessel or tissue or the like. Specifically, the balloon 12 is formed from metal or resin. It is preferable that at least the surface of the balloon 12 on which to provide the coating layer 30 is formed of resin. Examples of the material which can be used for forming at least the surface of the balloon 12 include thermoplastic resins such as polyolefins (e.g., polyethylene, polypropylene, polybutene, ethylene-propylene copolymers, ethylene-vinyl acetate copolymers, ionomers, or mixtures of two or more of the polyolefins), flexible polyvinyl chloride resin, polyamides, polyamide elastomers, nylon elastomers, polyester, polyester elastomers, polyurethane, fluororesins, etc., silicone rubbers, and latex rubbers. Among the thermoplastic resins, preferred are the polyamides. Specifically, at least part of the surface of the inflatable portion of the balloon to be coated with the drug is made of a polyamide. The polyamide is not particularly limited so long as it is a polymer which has an amide linkage. Examples of the polyamide include homopolymers such as polytetramethylene adipamide (nylon 46), polycaprolactam (nylon 6), polyhexamethylene adipamide (nylon 66), polyhexamethylene sebacamide (nylon 610), polyhexamethylene dodecamide (nylon 612), polyundecanolactam (nylon 11), polydodecanolactam (nylon 12), etc., copolymers such as caprolactam/lauryllactam copolymer (nylon 6/12), caprolactam/aminoundecanoic acid copolymer (nylon 6/11), caprolactam/ω-aminononanoic acid copolymer (nylon 6/9), caprolactam/hexamethylenediammonium adipate copolymer (nylon 6/66), etc., and aromatic polyamides such as copolymers of adipic acid with metaxylenediamine, or copolymers of hexamethylenediamine with m,p-phthalic acid. Further, polyamide elastomers as block copolymers in which nylon 6, nylon 66, nylon 11, nylon 12 or the like constitutes hard segments and a polyalkylene glycol, a polyether, an aliphatic polyester or the like constitutes soft segments can also be used as the base layer of the medical device according to the present disclosure. One of the aforesaid polyamides may be used singly. In addition, two or more of the aforesaid polyamides may be used in combination. Particularly, the balloon 12 preferably has a smooth surface of a polyamide.

Figure 3:
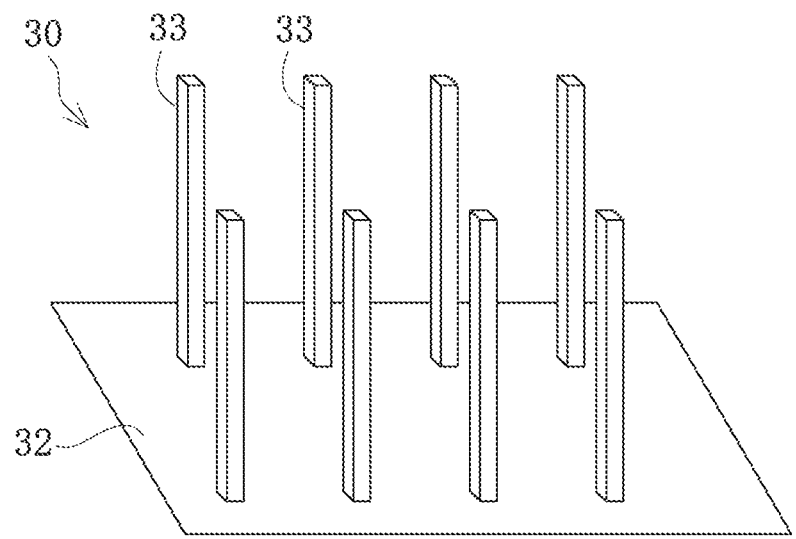
FIG. 3 is a schematic perspective view of elongate bodies composed of drug crystals on a surface of a balloon.
Figure 4:
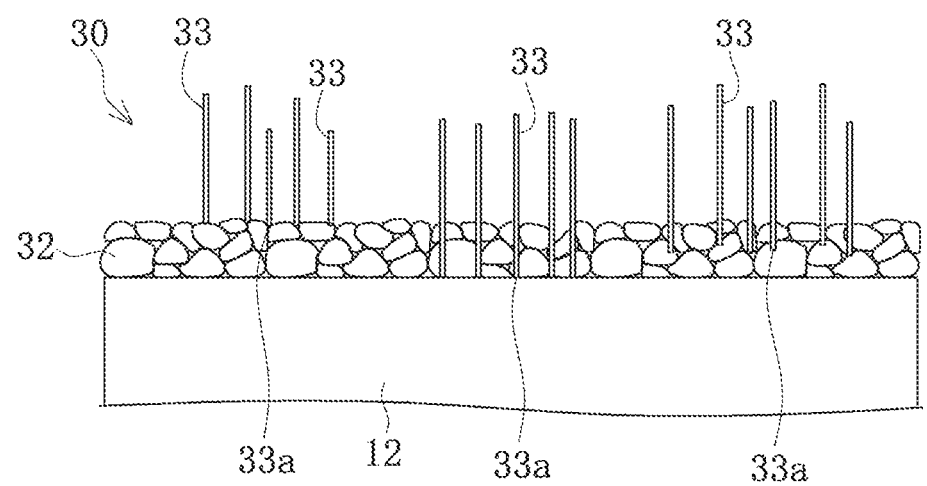
FIG. 4 is a schematic view of the elongate bodies composed of drug crystals and a base layer, on the surface of the balloon.

The balloon 12 is formed, on the surface of the balloon 12, with a coating layer 30, either directly or through a pretreatment layer such as a primer layer between the surface of the balloon 12 and the coating layer 30, by a method which will be described later. As depicted in FIGS. 3 and 4, the coating layer 30 includes a base layer 32 (excipient) that is disposed in a layer form on the surface 31 of the balloon 12 and that contains a water-soluble low-molecular compound, and a plurality of elongate bodies 33 which are crystals of a water-insoluble drug extending while having independent long axes. Such a form is referred to as the elongate bodies 33 in an independent state. On the other hand, as will be described later, depending on the formation conditions of the coating layer 30, the plurality of elongate bodies 33 may overlap with each other at a position in the longitudinal direction, and are united with one another to be in a state of aggregates, thereby forming crystal conjugates 38. In this case, they are referred to as the elongate bodies 33 in a non-independent state.

The amount of the drug contained in the coating layer 30 is not particularly limited; for example, the amount in density is 0.1 μg/mm² to 10 μg/mm², preferably 0.5 μg/mm² to 5 μg/mm², more preferably 0.5 μg/mm² to 3.5 μg/mm², and still more preferably 1.0 μg/mm² to 3 μg/mm². The amount of the crystals in the coating layer 30 is not particularly limited, and is, for example, 5 crystals/(10 μm²) to 500,000 crystals/(10 μm²) (the number of crystals per 10 μm²), preferably 50 crystals/(10 μm²) to 50,000 crystals/(10 μm²), and more preferably 500 crystals/(10 μm²) to 5,000 crystals/(10 μm²).

The elongate bodies 33 may be hollow (an annular space or lumen) or may be solid. Both hollow elongate bodies 33 and solid elongate bodies 33 may exist on the surface of the balloon 12. Where the elongate body 33 is hollow, at least a portion of the elongate body 33 near the tip end of the elongate body 33 is hollow. A section of the elongate body 33 in a plane perpendicular (orthogonal) to the long axis of the elongate body 33 has a void (hollow portion). In the elongate body 33 thus having a void, the section of the elongate body 33 in a plane perpendicular (orthogonal) to the long axis is polygonal in shape. The polygon here is, for example, a triangle, a tetragon, a pentagon, or a hexagon. Therefore, the elongate bodies 33 are each formed as an elongate polyhedron which has a distal end (or a distal surface) and a proximal end (or a proximal surface) and in which a side surface between the distal end (or the distal surface) and the proximal end (or the proximal surface) is composed of a plurality of substantially plain surfaces. In addition, the elongate bodies 33 may be needle-like in shape. This crystalline morphological form (hollow elongate body crystalline morphological form) constitutes the whole part or at least part of a plane, at the base layer surface.

The length in the axis direction of the elongate bodies 33 having the long axes is, for example, preferably 5 μm to 20 μm, more preferably 9 μm to 11 μm, and still more preferably around 10 μm. The diameter of the elongate bodies 33 having the long axes is preferably 0.01 μm to 5 μm, more preferably 0.05 μm to 4 μm, and still more preferably 0.1 μm to 3 μm. Examples of the combination of length in the axis direction and diameter of the elongate bodies 33 having the long axes include a combination of a diameter of 0.01 μm to 5 μm when the length is 5 μm to 20 μm, a combination of a diameter of 0.05 μm to 4 μm when the length is 5 μm to 20 μm, and a combination of a diameter of 0.1 μm to 3 μm when the length is 5 μm to 20 μm. The elongate bodies 33 having the long axes are substantially rectilinear in the long axis direction of the elongate bodies 33, and may also be curved in curved line forms. Both rectilinear elongate bodies 33 and curved elongate bodies 33 may exist on the surface of the balloon 12.

The elongate bodies 33 having the long axes after the coating and before the folding of the balloon 12 are formed not to lie flat but to stand in relation to the surface of the balloon 12. In the elongate bodies 33 in this instance, the angle of the elongate bodies 33 is changed by the pleating (the step of forming the balloon with the wing portions) or the folding (the step of folding the wing portions) of the balloon 12, whereby the angles of the long axes of the elongate bodies 33 relative to the surface of the balloon 12 can be changed. Therefore, while the crystals which are formed in the manner of lying flat on the surface of the balloon 12 from the beginning are firmly attached (fixed) to the surface of the balloon 12 and/or the adjacent elongate bodies 33, the elongate bodies 33 which are standing are not formed in the state of being physically fixed to the surface of the balloon 12 or the adjacent elongate bodies 33. For this reason, the standing elongate bodies 33 are only positioned (arranged) in such a manner as to make contact with, for example, the surface of the balloon 12 or the adjacent elongate bodies 33, and their positions can be changed on a three-dimensional basis. Accordingly, the elongate bodies 33 after the coating are formed such that their angles and positions can be changed through the pleating or folding of the balloon 12. Part of the elongate bodies 33 may be embedded in the surface of the balloon 12.

The base layer 32 is present in the state of being distributed into spaces between the plurality of elongate bodies 33 standing together. In regard of the proportions of the materials constituting the coating layer 30, the crystals of the water-insoluble drug preferably occupy a larger volume than that occupied by the base layer 32. The excipient constituting the base layer 32 does not form a matrix. The matrix is a layer which is configured by continuation of a comparatively high-molecular material (polymer or the like), which forms a network-like three-dimensional structure, and in which minute (i.e., extremely small) spaces are present. Therefore, the water-insoluble drug constituting the crystals is not adhered to the inside of a matrix material. Moreover, the water-insoluble drug constituting the crystals is not embedded in the matrix material. The base layer 32 may exist in a region where the elongate bodies 33 are present, and may not exist in a region where the elongate bodies 33 are absent.

The base layer 32 is formed as a dried layer, after being applied in an aqueous solution state to the surface of the balloon 12. The base layer 32 is amorphous. The base layer 32 may be crystal particles. The base layer 32 may exist as a mixture of an amorphous state with crystal particles. The base layer 32 in FIG. 4 is in a state including crystal particles and/or particulate amorphous portions. The base layer 32 is formed as a layer including the water-insoluble drug. Alternatively, the base layer 32 may be formed as an independent layer that does not include the water-insoluble drug. The thickness of the base layer 32 is, for example, 0.1 μm to 5 μm, preferably 0.3 μm to 3 μm, and more preferably 0.5 μm to 2 μm.

The drug in the coating on the surface of the balloon 12 may include an amorphous phase. The crystals and the amorphous phase may be disposed regularly in the coating layer 30. Alternatively, the crystals and the amorphous phase may be disposed irregularly.

The state of the elongate bodies 33, which are drug crystals, on the surface of the balloon 12 will be described further. As depicted in FIG. 3, in the state in which the elongate bodies 33 are formed, the elongate bodies 33 are in an erected state in relation to the surface of the balloon 12. On the other hand, by folding the balloon 12 and externally applying heat and a force to the surface, the elongate bodies 33 can be put into a tilted state and, further, crystal conjugates 38 can be formed in which the plurality of elongate bodies 33 are united to each other to form aggregates. That the elongate body 33 is in the tilted state means that the angle θ formed by the elongate body 33 relative to the surface of the balloon 12 is not more than 30 degrees, and that the elongate body 33 is in the erected state means that the angle θ is greater than 30 degrees.

Figure 5:
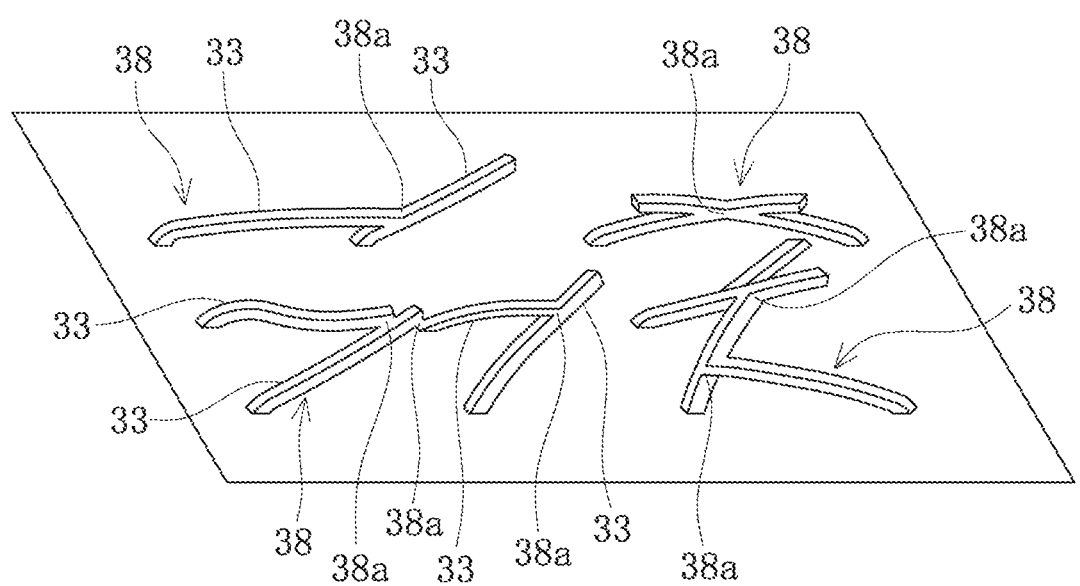
FIG. 5 is a schematic perspective view of crystal conjugates formed on the surface of the balloon.

As depicted in FIG. 5, the crystal conjugate 38 is formed of the elongate bodies 33 that overlap with each other at a position in the longitudinal direction and are joined to and united with one another. The number of the elongate bodies 33 which are joined to one another in the crystal conjugate 38 is two or more. A conjugate portion 38a, or a portion where the elongate bodies 33 are joined to each other in the crystal conjugate 38, is formed by fusing under heat applied to the elongate bodies 33 or by press bonding under a force exerted on the elongate bodies 33. In addition, the elongate bodies 33 forming the crystal conjugate 38 are in the tilted state relative to the surface of the balloon 12. The elongate bodies 33 in the tilted state means a state in which the angles θ formed by the elongate bodies relative to the surface of the balloon 12 are not more than 30 degrees, whereas the elongate bodies 33 in the erected state means a state other than the tilted state.

Figure 6A:
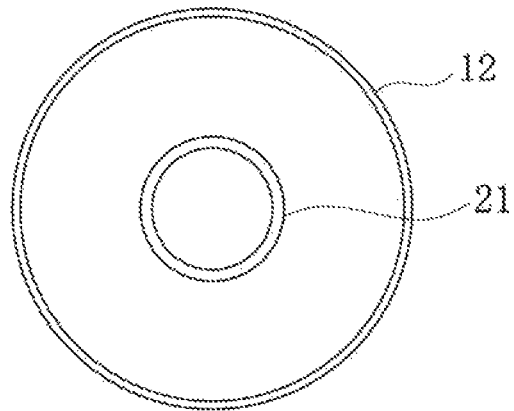
FIGS. 6A-6C are sectional views depicting a state before folding of a balloon (FIG. 6A), a state in which the balloon is formed with wing portions (FIG. 6B), and a folded state of the balloon (FIG. 6C).
Figure 6B:
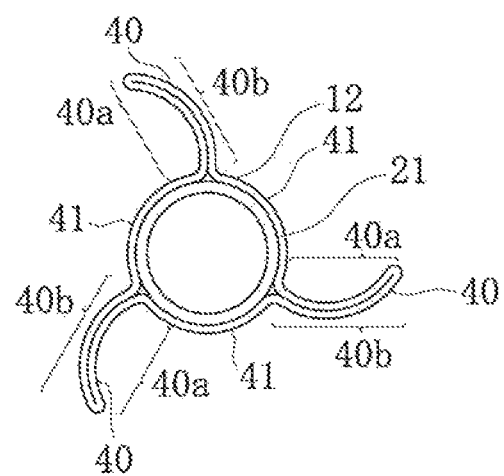

As depicted in FIG. 6A, the balloon 12 is substantially circular in sectional shape in a state in which an inflation fluid has been injected into the inside of the balloon 12. From this state, the balloon 12 is put into a state of having wing portions 40 as depicted in FIG. 6B, by a pleating section 120 which will be described later. In this state, the surface of the balloon 12 is divided into regions of circumferential surface portions 41 along the circumferential direction of the catheter shaft 11, and regions of the wing portions 40 projecting to the outer circumferential side. In addition, the wing portion 40 has a wing inner portion 40a which becomes a surface facing the circumferential surface portion 41 by being folded, and a wing outer portion 40b which becomes a surface facing the outer circumferential side by being folded. In this state, the elongate bodies 33 are in the tilted state in the regions of the wing inner portions 40a and the wing outer portions 40b, whereas the elongate bodies 33 are in the erected state in the regions of the circumferential surface portions 41.

Figure 6C:
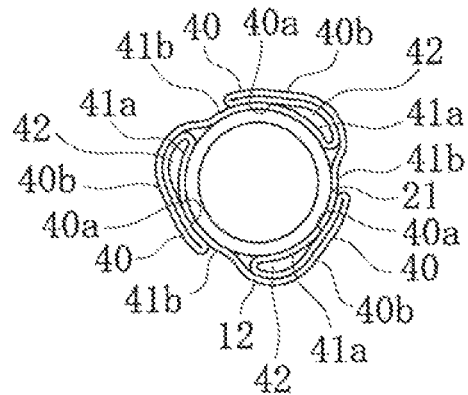

From the state of FIG. 6B, the balloon 12 is put into a folded state as depicted in FIG. 6C, by a folding section 130 which will be described later. In this state, the circumferential surface portions 41 are divided into facing surface portions 41a facing the wing inner portions 40a of the wing portions 40, and outer circumference constituting surface portions 41b facing the outer circumferential side. In addition, in the state in which the balloon 12 is folded, a root-side space portion 42 is formed between a root portion of the wing portion 40 and the circumferential surface portion 41. In the region of the root-side space portion 42, a minute gap (i.e., extremely small gap) is formed between the wing portion 40 and the circumferential surface portion 41. On the other hand, that region of the wing portion 40 which is on a tip side relative to the root-side space portion 42 is in the state of being in close contact with the circumferential surface portion 41. The proportion of the circumferential length of the root-side space portion 42 to the circumferential length of the wing portion 40 is, for example, in the range from 1% to 95%.

The balloon 12 is progressively inserted into a body lumen such as a blood vessel in the folded state of FIG. 6C, and is inflated at a lesion affected area to be put into the state of FIG. 6A. At the time of insertion of the balloon 12 into the body lumen, the surface of the balloon 12 is put into frictional contact with an inner wall surface of the body lumen. At least in those regions of the surface of the balloon 12 which are located at the wing outer portions 40b and the outer circumference constituting surface portions 41b both exposed to the outer circumferential side in the folded state, the crystal conjugates 38 as depicted in FIG. 5 are formed. The crystal conjugate 38 is composed of a plurality of elongate bodies 33 joined to and united with one another, and the elongate bodies 33 are each in a tilted state, so that the elongate bodies 33 are hardly separated from the surface of the balloon 12, even upon frictional contact with the inner wall surface of the body lumen. In other words, separation of the elongate bodies 33 during insertion of the balloon 12 can be restrained, and the drug can be effectively delivered to the lesion affected area.

Figure 7:
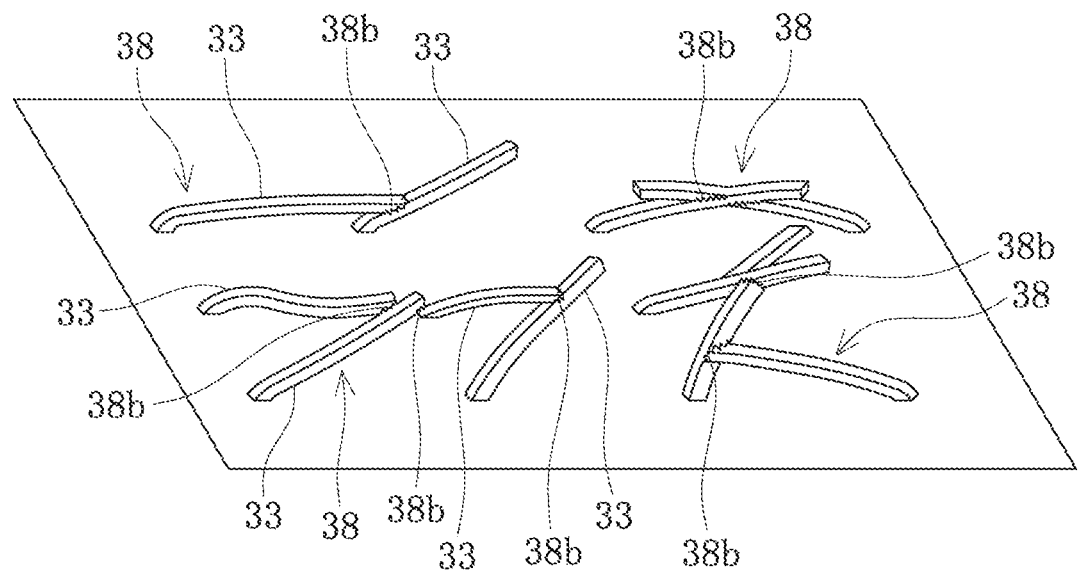
FIG. 7 is a schematic perspective view of crystal conjugates cracked upon inflation of the balloon.

When the balloon 12 is inflated at the lesion affected area, the distance between the elongate bodies 33 forming the crystal conjugate 38 is enlarged (i.e., increases), attendant on the expansion of the surface of the balloon 12. Therefore, the crystal conjugate 38 cannot maintain the state in which the elongate bodies 33 are joined to one another, and a crack 38b is generated in the conjugate portion 38a, as depicted in FIG. 7. Since the crystal conjugate 38 has the elongate bodies 33 overlapping with each other at a position in the longitudinal direction and being joined to and united with one another, the shapes of the elongate bodies 33 are left as they are, and the crystal conjugates 38 are liable to be separated upon inflation of the balloon 12. In addition, after the separation of the crystal conjugates 38, the elongate bodies 33 are in their elongate body form, so that the drug can be effectively transferred to the living body tissue. Note that while the cracks 38b are generated in the conjugate portions 38a in FIG. 7, the cracks may be generated in other portions of the elongate bodies 33.

Figure 8:
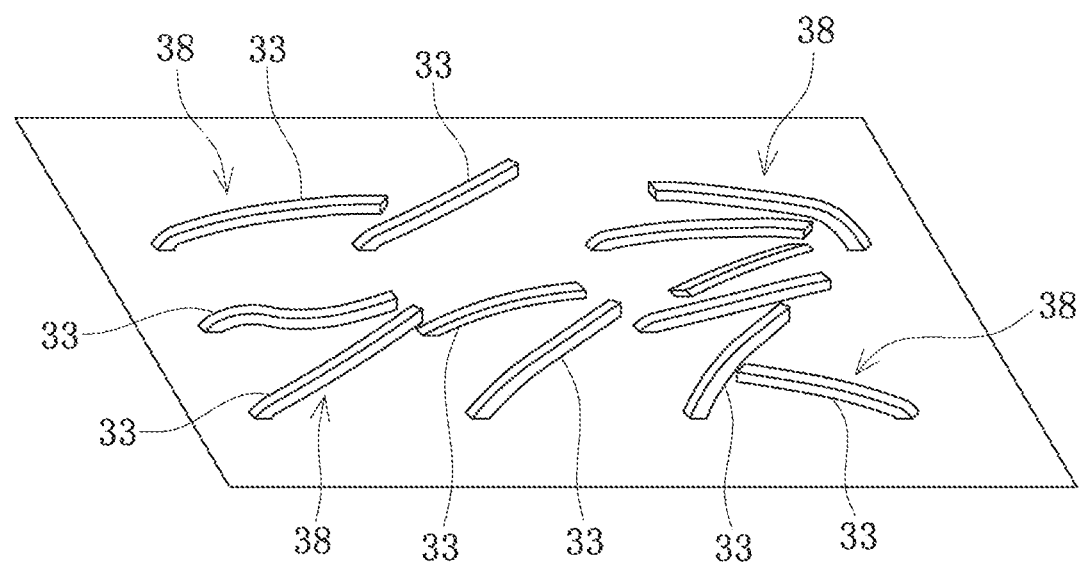
FIG. 8 is a schematic perspective view of elongate bodies put into an independent state by separation from the crystal conjugates upon inflation of the balloon.

When the balloon 12 is inflated further and the surface of the balloon 12 is expanded further, the elongate bodies 33 constituting the crystal conjugates 38 are separated at the positions of the cracks 38b, as depicted in FIG. 8, and are thus changed from the non-independent state into the independent state. While each of the elongated bodies 33 is separated as it is in the tilted state in FIG. 8, the elongate body 33 may be changed from the tilted state into the erected state, attendant on the expansion of the surface of the balloon 12. Attendant on the inflation of the balloon 12, the crystal conjugates 38 are separated into their respective elongate bodies 33, whereby transferability of the drug to the inner wall surface of the body lumen is improved, and the drug can be effectively transferred to the living body tissue.

In addition, with the elongate bodies 33 brought into the independent state from the crystal conjugates 38 in the non-independent state at the lesion affected area, toxicity in the living body can be lowered, and the stenosis inhibitory effect can be enhanced. In this case, since the unit of each of the crystals is reduced, the penetrating property into the tissue is good, and, since the elongate bodies 33 have good solubility, they act effectively and can restrain stenosis. In addition, it is considered that since the drug is less liable (or likely) to remain as large lumps (i.e., in a relatively large lump form) in the tissue, the drug exhibits low toxicity.

Thus, since the balloon 12 has on the surface of the balloon 12, the crystal conjugates 38 which are aggregates formed by joining together of the plurality of elongate bodies 33, separation of the elongate bodies 33 from the surface of the balloon 12 can be restrained during insertion of the balloon 12 into the body lumen. In addition, upon inflation of the balloon 12 at the lesion affected area, the crystal conjugates 38 are separated into the elongate bodies 33 which are in the independent state, and, therefore, transferability of the drug to the living body tissue can be improved.

Now, a balloon coating system for forming the coating layer 30 on the aforementioned balloon 12 will be described below. The present system includes a balloon coating apparatus 50 (see FIG. 9) for forming the coating layer 30 on the balloon 12, and a balloon folding apparatus 100 (see FIG. 11) for folding the balloon 12 formed with the coating layer 30. By use of the balloon coating apparatus 50, a plurality of elongate bodies which are crystals of a water-insoluble drug extending while having independent long axes are formed on a surface of the balloon 12. Thereafter, the balloon 12 is folded by the balloon folding apparatus 100, whereby the elongate bodies 33 are brought from the erected state into the tilted state in the axial direction in a partial region on the surface of the balloon 12.

Figure 9:
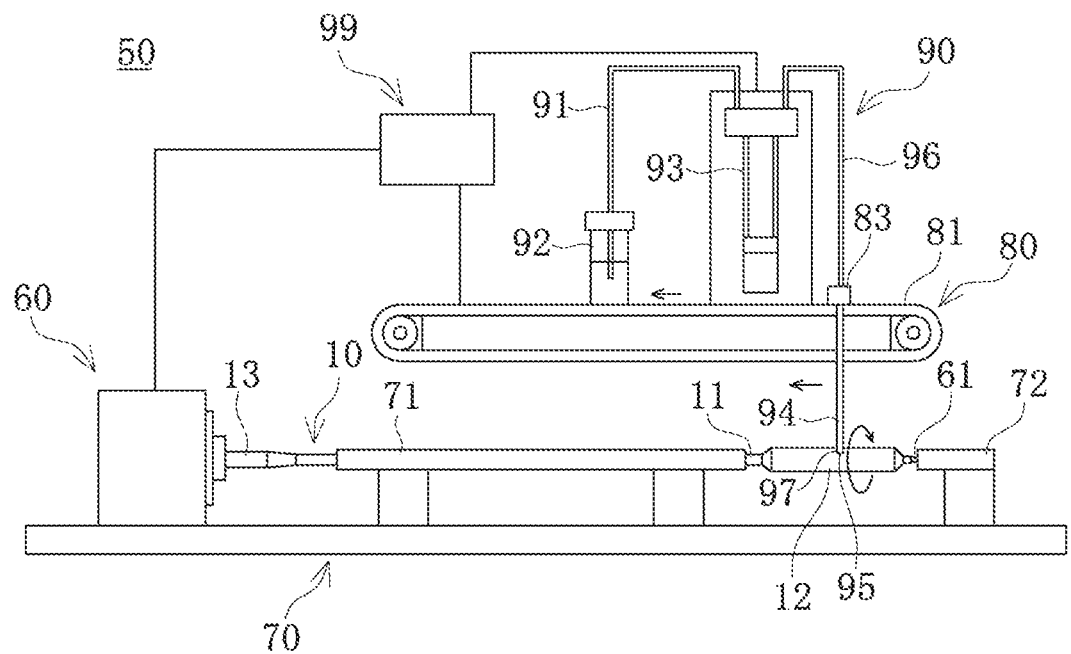
FIG. 9 is a schematic view of a balloon coating apparatus.
Figure 10:
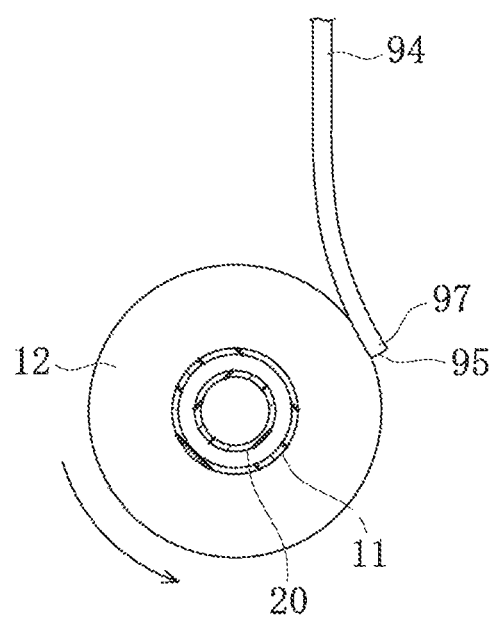
FIG. 10 is a sectional view of a dispensing tube in contact with the balloon.

In the first place, the balloon coating apparatus 50 will be described. As depicted in FIGS. 9 and 10, the balloon coating apparatus 50 includes a rotation mechanism section 60 for rotating the balloon catheter 10, and a support base 70 for supporting the balloon catheter 10. The balloon coating apparatus 50 further includes an application mechanism section 90 provided with a dispensing tube 94 for applying a coating solution to a surface of the balloon 12, a movement mechanism section 80 for moving the dispensing tube 94 relative to the balloon 12, and a control unit 99 for controlling the balloon coating apparatus 50.

The rotation mechanism section 60 holds the hub 13 of the balloon catheter 10, and rotates the balloon catheter 10 around an axis of the balloon 12 by a drive source, such as a motor, incorporated in the rotation mechanism section 60. The balloon catheter 10 is held, with a core member 61 inserted in the guide wire lumen 23, and the core member 61 helps prevent the coating solution from flowing into the guide wire lumen 23. In addition, for operating the flow of a fluid into the inflation lumen 22, a three-way cock (three-way valve) capable of operating the opening/closing of a passage or passages is connected to a proximal opening portion 13a of the hub 13 of the balloon catheter 10.

The support base 70 includes a pipe-shaped proximal-side support section 71 that accommodates the catheter shaft 11 in the support base 70 and rotatably supports the catheter shaft 11, and a distal-side support section 72 that rotatably supports the core member 61. Note that the distal-side support section 72 may, if possible, rotatably support a distal portion of the catheter shaft 11, instead of the core member 61.

The movement mechanism section 80 includes a movable base 81 which can be moved rectilinearly in a direction parallel to the axis of the balloon 12, and a tube fixing section 83 to which the dispensing tube 94 is fixed. The movable base 81 can be moved rectilinearly by a drive source, such as a motor, incorporated in the movable base 81. The tube fixing section 83 fixes an upper end of the dispensing tube 94 relative to the movable base 81. With the movable base 81 moved, therefore, the dispensing tube 94 is moved rectilinearly in a direction parallel to the axis of the balloon 12. In addition, the application mechanism section 90 is mounted on the movable base 81, and the movable base 81 moves the application mechanism section 90 rectilinearly in both directions (both senses) along the axis.

The application mechanism section 90 is a section that applies the coating solution to the surface of the balloon 12. The application mechanism section 90 includes a container 92 containing the coating solution, a feed pump 93 that feeds the coating solution at an arbitrary feed rate, and the dispensing tube 94 that applies the coating solution to the balloon 12.

The feed pump 93 is, for example, a syringe pump. Controlled by the control unit 99, the feed pump 93 can draw the coating solution from the container 92 through a suction tube 91, and feed the coating solution into the dispensing tube 94 through a supply tube 96 at an arbitrary feed rate. The feed pump 93 is disposed on the movable base 81, and can be moved rectilinearly by the movement of the movable base 81. Note that the feed pump 93 is not limited to the syringe pump so long as it can feed the coating solution, and may be, for example, a tube pump.

The dispensing tube 94 is a member which communicates with the supply tube 96 and discharges to the surface of the balloon 12 the coating solution supplied from the feed pump 93 through the supply tube 96. The dispensing tube 94 is a flexible circular pipe-shaped member. An upper end of the dispensing tube 94 is fixed to the tube fixing section 83, and extends downward in the vertical direction from the tube fixing section 83. The upper end of the dispensing tube 94 can be formed with an opening portion 95 at a discharge end 97 which is a lower end of the dispensing tube 94. With the movable base 81 moved, the dispensing tube 94 can be moved rectilinearly in both directions (both senses) along the axial direction of the balloon catheter 10, together with the feed pump 93 disposed on the movable base 81. The dispensing tube 94 can supply the coating solution to the surface of the balloon 12, in the state of being bent by being pressed against the balloon 12.

Note that the dispensing tube 94 may not necessarily be circular pipe-shaped so long as it can supply the coating solution. In addition, the dispensing tube 94 may not necessarily extend in the vertical direction so long as it can discharge the coating solution through the opening portion 95.

The dispensing tube 94 is preferably formed from a flexible material such that contact burden on the balloon 12 can be reduced and that variations in the contact position attendant on the rotation of the balloon 12 can be absorbed by flexure of the dispensing tube 94. Examples of the applicable material for the dispensing tube 94 include polyolefins such as polyethylene, polypropylene, etc., cyclic polyolefins, polyesters, polyamides, polyurethane, and fluororesins such as PTFE (polytetrafluoroethylene), ETFE (tetrafluoroethylene-ethylene copolymer), PFA (tetrafluoroethylene-perfluoroalkyl vinyl ether copolymer), FEP (tetrafluoroethylene-hexafluoropropylene copolymer), etc., but the material is not particularly limited so long as the material is flexible and deformable.

The outside diameter of the dispensing tube 94 is not particularly limited, and is, for example, 0.1 mm to 5.0 mm, preferably 0.15 mm to 3.0 mm, and more preferably 0.3 mm to 2.5 mm. The inside diameter of the dispensing tube 94 is not particularly limited, and is, for example, 0.05 mm to 3.0 mm, preferably 0.1 mm to 2.0 mm, and more preferably 0.15 mm to 1.5 mm. The length of the dispensing tube 94 is not particularly limited, and is preferably a length of not more than five times the balloon diameter, for example, 1.0 mm to 50 mm, preferably 3 mm to 40 mm, and more preferably 5 mm to 35 mm.

The control unit 99 is composed, for example, of a computer, and controls the rotation mechanism section 60, the movement mechanism section 80, and the application mechanism section 90. Therefore, the control unit 99 can control the rotating speed of the balloon 12, the moving speed of the dispensing tube 94 in the axial direction of the balloon 12, the drug discharge rate from the dispensing tube 94, and so on.

The coating solution supplied from the dispensing tube 94 to the balloon 12 is a solution or dispersion containing the constituent materials of the coating layer 30, and contains a water-insoluble drug, an excipient, an organic solvent, and water. After the coating solution is supplied to the surface of the balloon 12, the organic solvent and water volatilize, whereby a coating layer 30 including a plurality of elongate bodies 33 which are crystals of the water-insoluble drug extending in the longitudinal direction is formed on the surface of the balloon 12. The viscosity of the coating solution is 0.5 cP to 1,500 cP, preferably 1.0 cP to 500 cP, and more preferably 1.5 cP to 100 cP.

The water-insoluble drug means a drug which is insoluble or difficultly soluble in water; specifically, the water-insoluble drug is a drug of which the solubility in water is less than 5 mg/mL at pH 5 to 8. The solubility may be less than 1 mg/mL, or, further, may be less than 0.1 mg/mL. The water-insoluble drug includes fat-soluble drugs.

Some preferred examples of the water-insoluble drug include immunosuppressants, for example, cyclosporines inclusive of cyclosporine, immunoadjuvants such as rapamycin, carcinostatics such as paclitaxel, antiviral or antibacterial agents, antineoplastic agents, analgesic and anti-inflammatory agents, antibiotics, antiepileptics, anxiolytic agents, antiparalytic agents, antagonists, neuron blocking agents, anticholinergic and cholinergic agents, muscarine antagonists and muscarine agents, antiadrenergic agents, antiarrhythmic agents, antihypertensive agents, hormone preparations, and nutritional supplements.

The water-insoluble drug is preferably at least one selected from a group composed of rapamycin, paclitaxel, docetaxel, and everolimus. The rapamycin, paclitaxel, docetaxel and everolimus herein include their analogs and/or derivatives so long as the analogs and/or derivatives have equivalent drug activity to the original. For example, paclitaxel and docetaxel are in an analog relation. Rapamycin and everolimus are in a derivative relation. Among the water-insoluble drugs, more preferable is paclitaxel.

The excipient constitutes the base layer 32 on the balloon 12. The excipient includes a water-soluble low-molecular compound. The molecular weight of the water-soluble low-molecular compound, for example, is 50 to 2,000, preferably 50 to 1,000, more preferably 50 to 500, and still more preferably 50 to 200. The amount of the water-soluble low-molecular compound is preferably 5 parts by mass to 10,000 parts by mass, more preferably 5 parts by mass to 200 parts by mass, and still more preferably 8 parts by mass to 150 parts by mass, per 100 parts by mass of the water-insoluble drug. Examples of the applicable constituent material of the water-soluble low-molecular compound include serine ethyl ester, citric acid esters, polysorbates, water-soluble polymers, sugars, contrast agents, amino acid esters, glycerol esters of short-chain monocarboxylic acids, pharmaceutically acceptable salts and surfactants, and mixtures of two or more of the water-soluble low-molecular compounds. The water-soluble low-molecular compound is characterized in that it has a hydrophilic group and a hydrophobic group and is soluble in water. Preferably, the water-soluble low-molecular compound is non-swellable or difficultly swellable. The excipient is preferably amorphous on the balloon 12. The excipient including the water-soluble low-molecular compound has an effect of uniformly dispersing the water-insoluble drug on the surface of the balloon 12. The excipient constituting the base layer 32 is preferably not a hydrogel. Being the low-molecular compound, the base layer 32 is rapidly dissolved without being swelled upon contact with an aqueous solution. Further, since the base layer 32 becomes easily soluble upon inflation of the balloon 12 in a blood vessel, the elongate bodies 33 of the water-insoluble drug on the surface of the balloon 12 become easily releasable; thus, the base layer 32 has an effect of increasing the amount of the drug adhered to the blood vessel. In the case where the base layer 32 is a matrix composed of a contrast agent such as Ultravist®, the crystal particles are embedded in the matrix, and crystals are not produced to extend from the substrate of the balloon 12 toward the outside of the matrix. On the other hand, the elongate bodies 33 according to the present embodiment extend from the surface of the substrate of the balloon 12 to the outside of the base layer 32. The length of that portion of the elongate body 33 which is located on the outside of the base layer 32 is greater than the length of that portion of the elongate body 33 which is located inside the base layer 32. The base layer 32 is formed in such a manner as to support the base portions 33a of the elongate bodies 33 which are crystals.

The organic solvent is not particularly limited, and examples of the organic solvent include tetrahydrofuran, acetone, glycerin, ethanol, methanol, dichloromethane, hexane, ethyl acetate, and water. Among the organic solvents, for example, preferred are mixed solvents of some of tetrahydrofuran, ethanol, acetone, and water. Examples of the preferred mixed solvents include a mixture of tetrahydrofuran and water, a mixture of tetrahydrofuran and ethanol and water, a mixture of tetrahydrofuran and acetone and water, a mixture of acetone and ethanol and water, and a mixture of tetrahydrofuran and acetone and ethanol and water.

Now, a method of forming crystals of the water-insoluble drug on the surface of the balloon 12 by use of the aforementioned balloon coating apparatus 50 will be described below.

First, the inflation fluid is supplied into the balloon 12 through the three-way cock (three-way value) connected to the proximal opening portion 13a of the balloon catheter 10. Next, in a state where the balloon 12 is inflated, the three-way cock is operated to seal up the inflation lumen 22, thereby maintaining the balloon 12 in the inflated state. The balloon 12 is inflated with a pressure (e.g., 4 atm) lower than a pressure (e.g., 8 atm) at the time of use in a blood vessel. Note that the coating layer 30 can also be formed on the surface of the balloon 12 without inflating the balloon 12, and, in that case, it is unnecessary to supply the inflation fluid into the balloon 12.

Subsequently, in a state in which the dispensing tube 94 does not make contact with the surface of the balloon 12, the balloon catheter 10 is rotatably disposed on the support base 70, and the hub 13 is interlocked with the rotation mechanism section 60.

Next, the position of the movable base 81 is adjusted to position the dispensing tube 94 in relation to the balloon 12. In this instance, the dispensing tube 94 is positioned to a position on the most distal side on the balloon 12 where to form the coating layer 30. As an example, the extending direction (discharge direction) of the dispensing tube 94 is opposite to the rotating direction of the balloon 12. Therefore, at the position where the dispensing tube 94 is put in contact with the balloon 12, the balloon 12 is rotated in the direction opposite to the discharge direction in which the coating solution is discharged from the dispensing tube 94. By this, a stimulus can be given to the coating solution, whereby formation of nuclei of the drug crystal can be promoted. Since the extending direction (discharge direction) of the dispensing tube 94 toward the opening portion 95 is opposite to the rotating direction of the balloon 12, the crystals of the water-insoluble drug formed on the surface of the balloon 12 are liable to be formed including a morphological form in which the crystals include a plurality of elongate bodies having mutually independent long axes. Note that the extending direction of the dispensing tube 94 may not necessarily be opposite to the rotating direction of the balloon 12, and, hence, may be the same as or perpendicular to the rotating direction.

Subsequently, the coating solution is supplied to the dispensing tube 94 while adjusting the feed rate by the feed pump 93, the balloon catheter 10 is rotated by the rotation mechanism section 60, and the movable base 81 is moved so that the dispensing tube 94 is gradually moved proximally along the axial direction of the balloon 12. The coating solution discharged from the opening portion 95 of the dispensing tube 94 is applied to the outer circumferential surface of the balloon 12 while drawing a spiral, since the dispensing tube 94 is moved relative to the balloon 12.

The moving speed of the dispensing tube 94 is not particularly limited, and is, for example, 0.01 mm/second to 2 mm/second, preferably 0.03 mm/second to 1.5 mm/second, and more preferably 0.05 mm/second to 1.0 mm/second. The discharge rate of the coating solution from the dispensing tube 94 is not particularly limited, and is, for example, 0.01 µL/second to 1.5 µL/second, preferably 0.01 µL/second to 1.0 µL/second, and more preferably 0.03 µL/second to 0.8 µL/second. The rotating speed of the balloon 12 is not particularly limited, and is, for example, 10 rpm to 300 rpm, preferably 30 rpm to 250 rpm, and more preferably 50 rpm to 200 rpm. The diameter of the balloon 12 when coated with the coating solution is not particularly limited, and is, for example, 1 mm to 10 mm, preferably 2 mm to 7 mm.

Thereafter, the organic solvent contained in the coating solution applied to the surface of the balloon 12 volatilizes earlier than water. Therefore, the organic solvent volatilizes in a condition where the water-insoluble drug, the water-soluble low-molecular compound and water are left on the surface of the balloon 12. When the organic solvent thus volatilizes with water left in the coating, the water-insoluble drug is precipitated inside the water-soluble low-molecular compound that contains water, and crystals gradually grow from crystal nuclei, so that drug crystals of a morphological form in which the crystals include a plurality of elongate bodies 33 having mutually independent long axes are formed on the surface of the balloon 12. Note that the elongate bodies 33 in this state are in the erected state. The base ends of the elongate bodies 33 may be located on the surface of the balloon 12, on the surface of the base layer 32, or in the inside of the base layer 32 (see FIG. 4). After the organic solvent has volatilized and the drug crystals are precipitated as the plurality of elongate bodies 33, water evaporates more slowly than the organic solvent, and the base layer 32 including the water-soluble low-molecular compound is formed. The time taken for evaporation of water is appropriately set in accordance with the kind of the drug, the kind of the water-soluble low-molecular compound, the kind of the organic solvent, the ratios of the amounts of the materials, the coating amount of the coating solution, and the like, and is, for example, approximately 1 second to 600 seconds.

Then, while rotating the balloon 12, the dispensing tube 94 is gradually moved in the axial direction of the balloon 12, whereby the coating layer 30 is gradually formed on the surface of the balloon 12 along the axial direction of the balloon 12. After the coating layer 30 including the elongate bodies 33 is formed over the whole range of coating for the balloon 12, operations of the rotation mechanism section 60, the movement mechanism section 80 and the application mechanism section 90 are stopped.

Thereafter, the balloon catheter 10 is removed from the balloon coating apparatus 50, to complete the coating of the balloon 12.

Now, the balloon folding apparatus 100 will be described below. The balloon folding apparatus 100 is an apparatus capable of folding the balloon 12 in the manner of winding around the inner tube 21.

Figure 11:
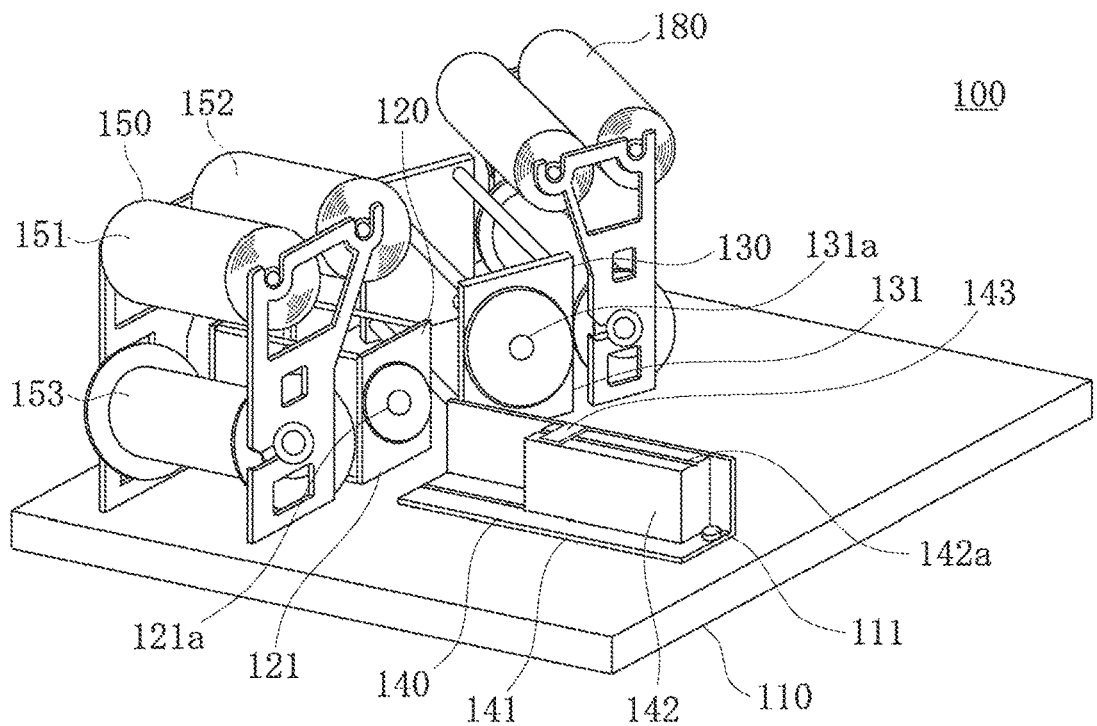
FIG. 11 is a perspective view of a balloon folding apparatus.

As depicted in FIG. 11, the balloon folding apparatus 100 has a pleating section 120, a folding section 130 and a support base 140 which are disposed on a base 110 formed in a base shape. The pleating section 120 is capable of forming the balloon 12 with wing portions 40 projecting in radial directions. The folding section 130 is capable of folding the wing portions 40 formed in the balloon 12, in the manner of lying flat in the circumferential direction. The support base 140 is capable of mounting and holding the balloon catheter 10 thereon. The wing portions 40 formed in the balloon 12 are formed by pleats extending substantially in an axial direction of the balloon 12, such that the pleats project in the circumferential direction from a long axis of the balloon 12 when viewed in a section perpendicular to the axis of the balloon 12. The length in the long axis direction of the wing portions 40 does not exceed the length of the balloon 12. The length of the wing portions 40 in the direction of projecting in the circumferential direction of the catheter shaft 11 is, for example, 1 mm to 8 mm. The number of the wing portions 40 is not particularly limited, it can be selected from among two, three, four, five, six and seven, and it is three in the present embodiment.

On the base 110, a film supply section 150 that supplies a first film 155 and a second film 156 to the pleating section 120 is disposed adjacently to the pleating section 120. In addition, on the base 110, a film supply section 180 that supplies a first film 181 and a second film 182 to the folding section 130 is disposed adjacently to the folding section 130.

The pleating section 120 has a front surface plate 121 perpendicular to the base 110, and the front surface plate 121 has an insertion hole 121a into which a distal portion of the balloon catheter 10 can be inserted. In addition, the folding section 130 has a front surface plate 131 perpendicular to the base 110, and the front surface plate 131 has an insertion hole 131a into which the distal portion of the balloon catheter 10 can be inserted. The front surface plate 131 of the folding section 130 faces in a direction different by a predetermined angle from the direction in which the front surface plate 121 of the pleating section 120 faces.

On that side of the support base 140 which is remote from the pleating section 120 and the folding section 130, a support shaft 111 projecting upward from the base 110 is pivotally mounted. The support base 140, by sliding movement on an upper surface of the base 110 with the support shaft 111 as a center, can be positioned in a position for facing the front surface plate 121 of the pleating section 120 and a position for facing the front surface plate 131 of the folding section 130.

The support base 140 has a base section 141 mounted on the base 110, and a holding base section 142 horizontally movable on the base section 141. The base section 141 is slidable on the upper surface of the base 110. The holding base section 142 can be advanced or retracted in relation to (in regard of a direction toward) the pleating section 120 or the folding section 130, by sliding movement on the upper surface of the base section 141.

An upper surface of the holding base section 142 is formed with a groove-shaped mounting section 142a on which the catheter shaft 11 of the balloon catheter 10 can be mounted. In addition, the holding base section 142 is provided with a holding section 143 for holding the catheter shaft 11 mounted on the mounting section 142a. Note that the balloon catheter 10 may be fixed by other methods so long as the balloon catheter 10 can be fixed.

In a state in which the support base 140 faces the front surface plate 121 of the pleating section 120, the center of the insertion hole 121a formed in the front surface plate 121 is located on an extension line of the mounting section 142a of the holding base section 142. Therefore, the balloon catheter 10 with the catheter shaft 11 mounted on the mounting section 142a is inserted into the inside of the pleating section 120 through the center position of the insertion hole 121a. In a state in which the support base 140 faces the front surface plate 131 of the folding section 130, the center of the insertion hole 131a formed in the front surface plate 131 is located on an extension line of the mounting section 142a of the holding base section 142. Therefore, the balloon catheter 10 with the catheter shaft 11 mounted on the mounting section 142a is inserted into the inside of the folding section 130 through the center position of the insertion hole 131a, by sliding movement of the holding base section 142 on the base section 141.

Figure 12:
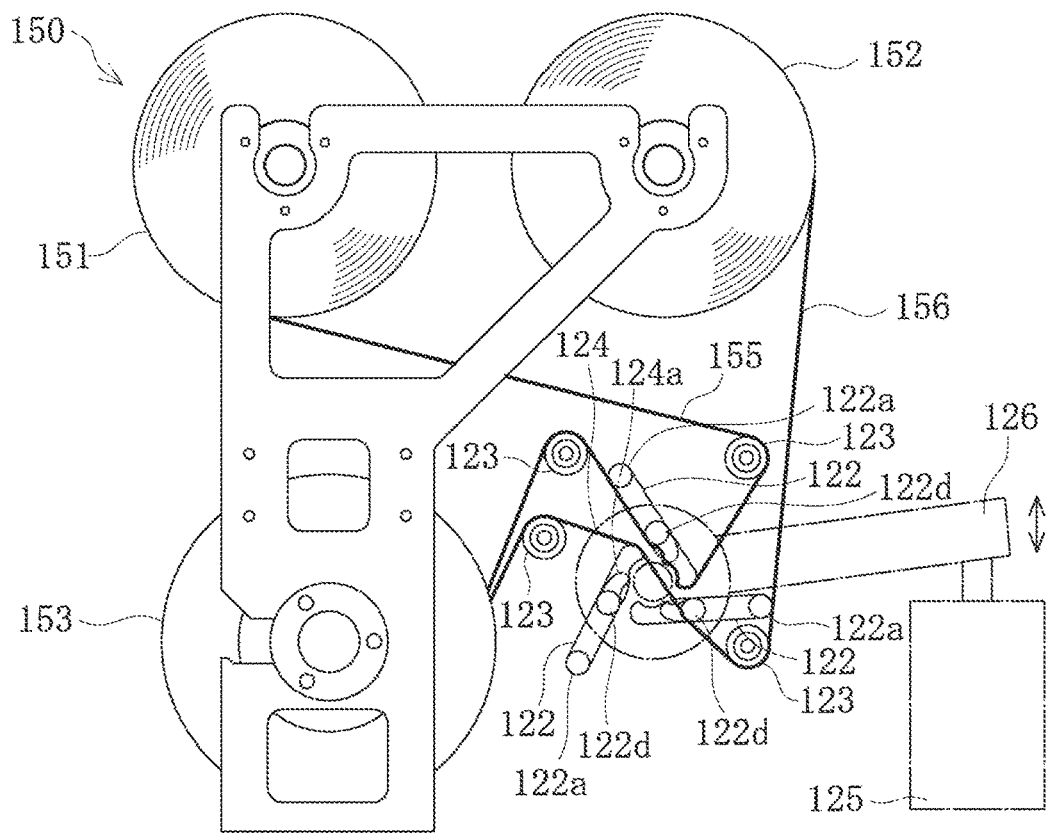
FIG. 12 is a front view depicting the layout of blades and a film supply section of a pleating section.

Now, the structure of the pleating section 120 will be described below. As depicted in FIG. 12, the pleating section 120 has three wing-forming blades 122 in the inside of the pleating section. Each of the blades 122 is a plate-shaped member formed to have an equal sectional shape at positions along the axial direction of the balloon catheter 10 inserted. The blades 122 are disposed at mutual angles of 120 degrees, with the center position of insertion of the balloon 12 as a reference. In other words, the blades 122 are disposed at regular angular intervals along the circumferential direction. The blade 122 has a rotary movement center portion 122a near an outer circumferential end of the blade 122, and can be moved rotationally around the rotary movement center portion 122a. In addition, the blade 122 has a moving pin 122d extending in the axial direction, on the inner circumference side relative to the rotary movement center portion 122a. The moving pin 122d is fitted in a fitting groove 124a formed in a rotary member 124 which is rotatable inside the pleating section 120. The rotary member 124 is interlocked with a beam section 126 extending substantially horizontally. The rotary member 124 can be moved rotationally by receiving a rotating force from the beam section 126 which is inclined by receiving a force from a drive source 125 such as a hydraulic cylinder or a motor. When the rotary member 124 is rotated, the moving pins 122d fitted in the fitting grooves 124a are moved in the circumferential direction, whereby each of the blades 122 is moved rotationally around the rotary movement center portion 122a of the rotary member 124. With the three blades 122 moved rotationally, a space region in a central area surrounded by the blades 122 can be narrowed. Note that the number of the blades 122 is not particularly limited so long as it is not less than two.

Figure 13:
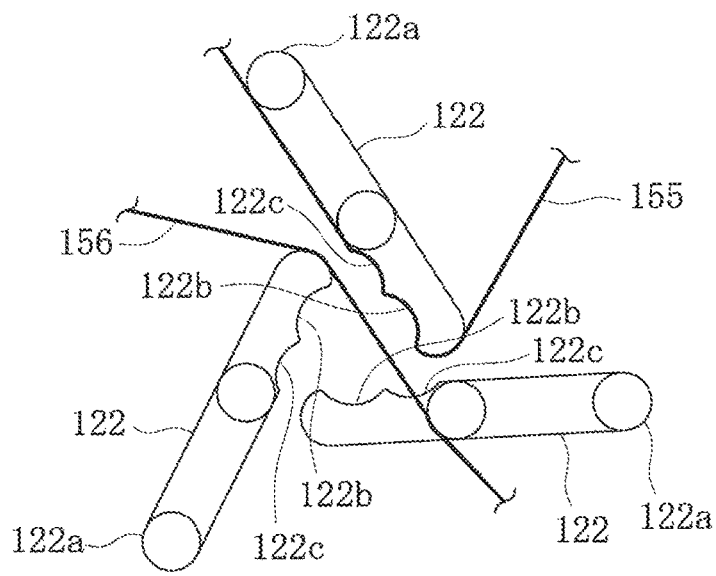
FIG. 13 is a front view of the blades in the pleating section.

The blade 122 has a first shape forming portion 122b and a second shape forming portion 122c, which are substantially arcuate in shape, at inner circumferential end portions of the blade 122 on the side opposite to its rotary movement center portion 122a as depicted in FIG. 13. As the blade 122 is moved rotationally, the first shape forming portion 122b comes into contact with a surface of the balloon 12 inserted in the pleating section 120, whereby the balloon 12 can be formed with the wing portion 40 projecting in a radial direction. As the blade 122 is moved rotationally, the second shape forming portion 122c comes into contact with the wing portion 40 formed in the balloon 12, whereby the wing portion 40 can be curved in a predetermined direction. In addition, the pleating section 120 has a heater (not depicted) for heating the blades 122. The length of the blade 122 along the axial direction of the balloon catheter 10 is greater than the length of the balloon 12. In addition, the lengths of the first shape forming portion 122b and the second shape forming portion 122c of the blade 122 may range or may not range over the whole length of the blade 122.

The blades 122 are supplied from the film supply section 150 with the first film 155 and the second film 156 which are made of resin. For guiding each of the films, a plurality of rotary shaft portions 123 are provided in the pleating section 120. The first film 155 is passed from a first film holding section 151 and through the rotary shaft section 123, to be engaged on a surface of the blade 122 disposed at an upper portion. In addition, the first film 155 is passed from the blade 122 and through the rotary shaft section 123, to reach a film take-up section 153 which is rotationally driven by a drive source such as a motor not depicted. The second film 156 is passed from a second film holding section 152 and through the rotary shaft section 123, to be engaged on the two blades 122 disposed at lower portions. In addition, the second film 156 is passed through the rotary shaft section 123, to reach the film take-up section 153. By these, a state is established in which the center position of the pleating section 120 in which the balloon 12 is inserted and passed is surrounded by the first film 155 and the second film 156.

The first film 155 and the second film 156 have a function of protecting the balloon 12 by preventing the balloon 12 from making direct contact with the surfaces of the blades 122 when the balloon 12 is inserted into the pleating section 120 and the blades 122 are moved rotationally to form the balloon 12 with the wing portions 40. After the wing portions 40 of the balloon 12 are formed, the first film 155 and the second film 156 are taken up onto the film take-up section 153 by a predetermined length. In other words, those portions of the first film 155 and the second film 156 which have once made contact with the balloon 12 do not make contact with the balloon 12 again, and, each time the balloon 12 is inserted, new portions of the films are supplied to the center position of the pleating section 120.

As depicted in FIG. 13, in a state before the insertion of the balloon 12, the first shape forming portions 122b and the second shape forming portions 122c of the three blades 122 are spaced from one another. A central region among the blades 122 is surrounded by the first shape forming portions 122b which are substantially arcuate in shape, and the balloon 12 before folded can be inserted in the central region.

Figure 14:
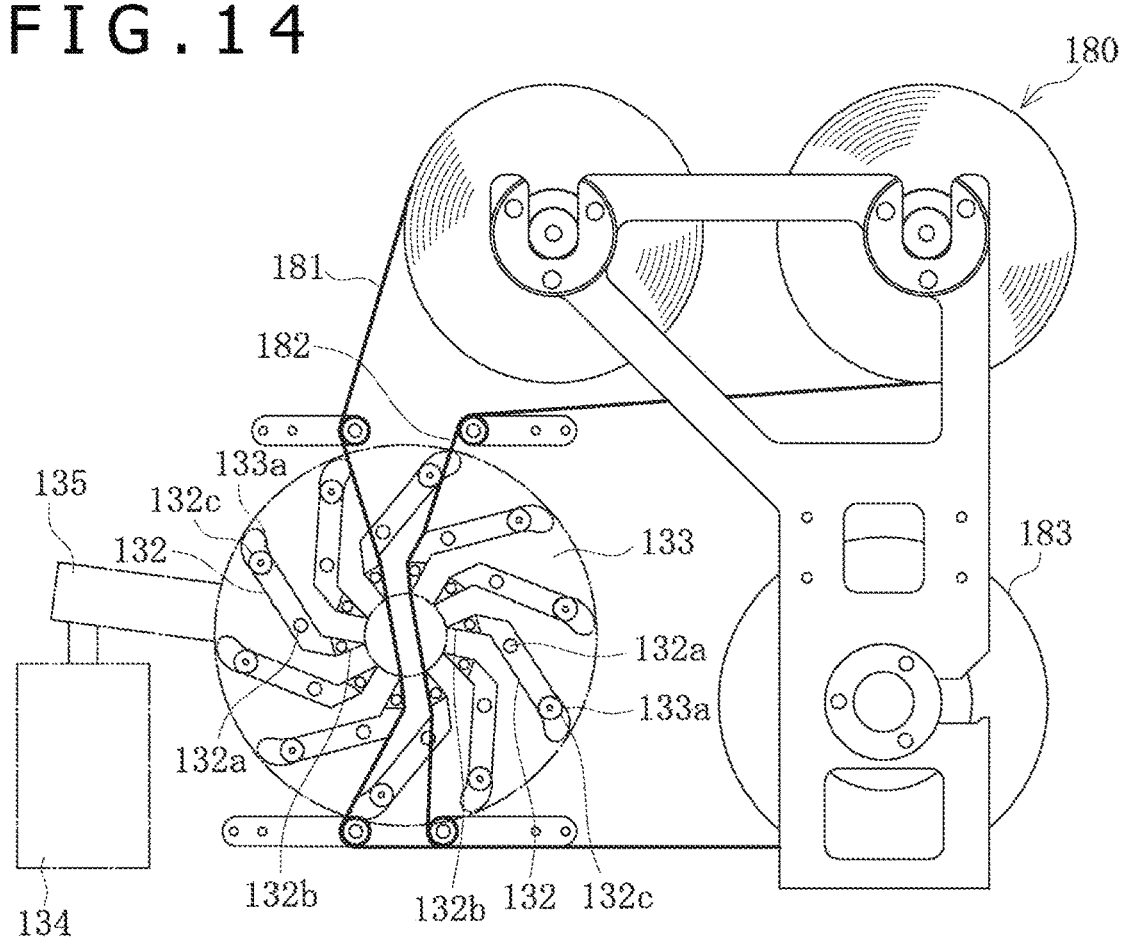
FIG. 14 is a front view depicting the layout of blades and a film supply section of a folding section.

Now, the structure of the folding section 130 will be described below. As depicted in FIG. 14, the folding section 130 has ten wing-folding blades 132 in the inside of the folding section 130. Each of the blades 132 is a plate-shaped member formed to have an equal sectional shape at positions along the axial direction of the balloon catheter 10 inserted. The blades 132 are disposed at mutual angles of 36 degrees, with the center position of insertion of the balloon 12 as a reference. In other words, the blades 132 are disposed at regular angular intervals along the circumferential direction. The blade 132 has a rotary movement center portion 132a near its center, and can be moved rotationally around the rotary movement center portion 132a. In addition, each blade 132 has a moving pin 132c extending in the axial direction, near its outer circumferential end. The moving pin 132c is fitted in a fitting groove 133a formed in a rotary member 133 which is rotatable inside the folding section 130. The rotary member 133 is interlocked with a beam 135 extending substantially horizontally. The rotary member 133 can be moved rotationally by receiving a rotating force from the beam 135 which is inclined by receiving a force from a drive source 134 such as a hydraulic cylinder or a motor. When the rotary member 133 is rotated, the moving pins 132c fitted in the fitting grooves 133a are moved in the circumferential direction, whereby each of the blades 132 is moved rotationally around the rotary movement center portion 132a of the rotary member 133. With the ten blades 132 moved rotationally, a space region in a central area surrounded by the blades 132 can be narrowed. Note that the number of the blades 132 is not limited to ten.

The blade 132 is bent on a tip side, and a tip portion 132b of the blade 132 is sharp (i.e., having an edge or point) in shape. As the blades 132 are moved rotationally, the tip portions 132b come into contact with the surface of the balloon 12 inserted into the folding section 130, whereby the wing portions 40 formed in the balloon 12 can be folded in the manner of lying flat in the circumferential direction. In addition, the folding section 130 has a heater (not depicted) for heating the blades 132.

The blades 132 are supplied from the film supply section 180 with the first film 181 and the second film 182 which are made of resin. A supplying structure for each film is the same as that in the case of the pleating section 120. The first film 181 and the second film 182 are disposed to face each other such that a central space region surrounded by the blades 132 is interposed between the first film 181 and the second film 182. By the first film 181 and the second film 182, the balloon 12 inserted in the folding section 130 can be prevented from making direct contact with the surfaces of the blades 132. The first film 181 and the second film 182 are passed through the blades 132, to reach a film take-up section 183 which is rotationally driven by a drive source such as a motor not depicted.

Figure 15:
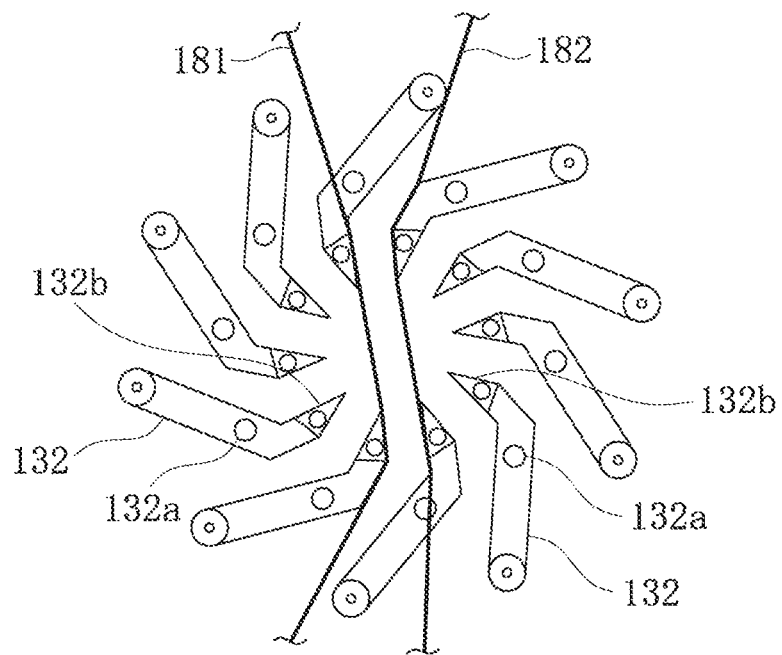
FIG. 15 is a front view of the blades in the folding section.

As depicted in FIG. 15, in a state before insertion of the balloon 12, the tip portions 132b of the blades 132 are in the state of being spaced from one another in the circumferential direction. In a central region which is surrounded by the blades 132 and is located between the first film 181 and the second film 182, the balloon 12 formed with the wing portions 40 can be inserted.

Now, a method of folding the balloon 12 formed on its surface with crystals of a drug by the balloon coating apparatus 50, by use of the balloon folding apparatus 100, will be described below.

First, for forming the balloon 12 with the wing portions 40, the catheter shaft 11 is mounted on the mounting section 142a of the support base 140 and is held by the holding section 143. An inflation fluid is injected into the balloon 12 through the three-way cock (three-way valve) attached to the hub 13, the hub 13 and the inner tube 21, whereby the balloon 12 is put into a little inflated state. In addition, the blades 122 in the pleating section 120 are heated. The core member 61 is inserted in the guide wire lumen 23. By the core member 61, the catheter shaft 11 is restrained from flexure due to the weight of the catheter shaft 11.

Figure 16:
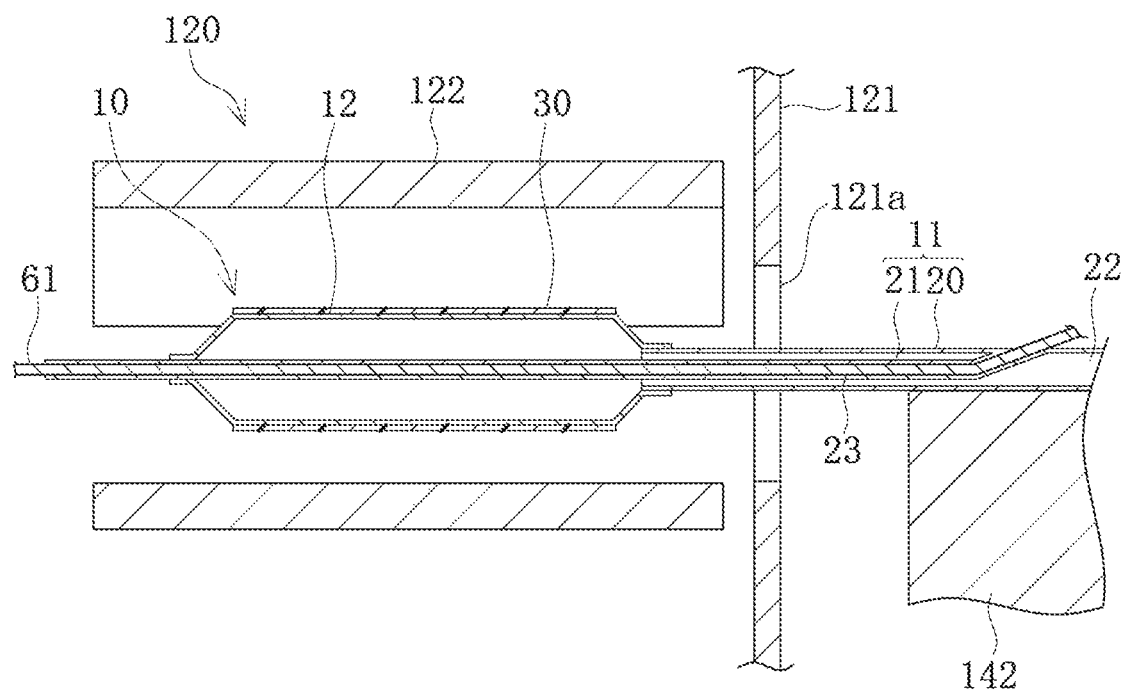
FIG. 16 is a sectional view of a balloon catheter disposed in the pleating section.

Next, as depicted in FIG. 16, the holding base section 142 is moved sliding on the base section 141, to insert the balloon catheter 10 into the pleating section 120 through the insertion hole 121a.

Subsequently, the drive source 125 is operated to rotate the rotary member 124 (see FIG. 12), whereon as depicted in FIG. 15, the blades 122 are moved rotationally, and the first shape forming portions 122b of the blades 122 approach one another, so that the central region among the blades 122 is narrowed. Attendant on this, the balloon 12 inserted in the central region among the blades 122 is pressed against the inner tube 22 by the first shape forming portions 122b. That portion of the balloon 12 which is not pressed by the first shape forming portion 122b is pushed out into a gap between a tip portion of one blade 122 and the second shape forming portion 122c of the blade 122 adjacent to the one blade 122, whereby the wing portion 40 curved to one side is formed. Since the balloon 12 is heated to approximately 50 degrees to 60 degrees by the blades 122, the wing portions 40 thus formed can maintain their shapes. In this way, the balloon 12 is formed with three wing portions 40 along the circumferential direction.

In this instance, those surfaces of each blade 122 which make contact with the balloon 12 are covered by the first film 155 and the second film 156, so that the balloon 12 does not make direct contact with the surfaces of the blades 122.

Figure 17:
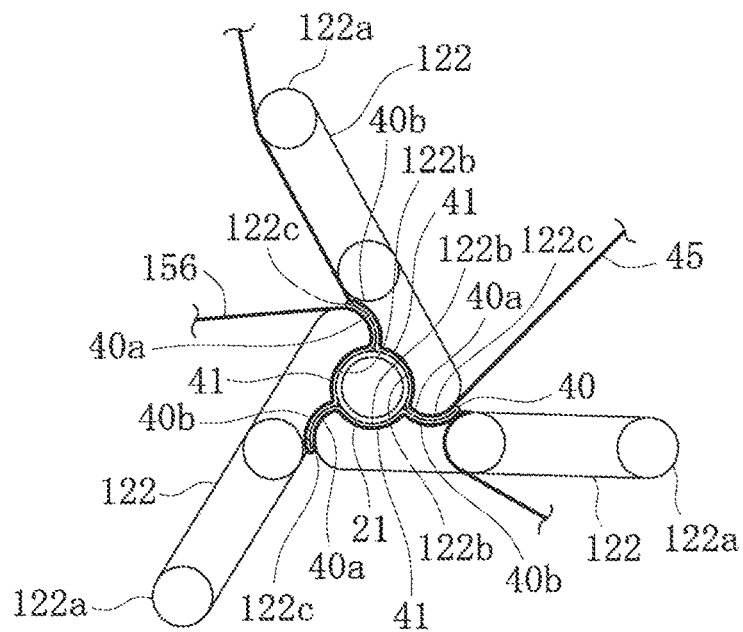
FIG. 17 is a front view depicting the blades in the pleating section in a state in which the balloon is formed with wing portions by rotationally moving the blades.
Figure 18:
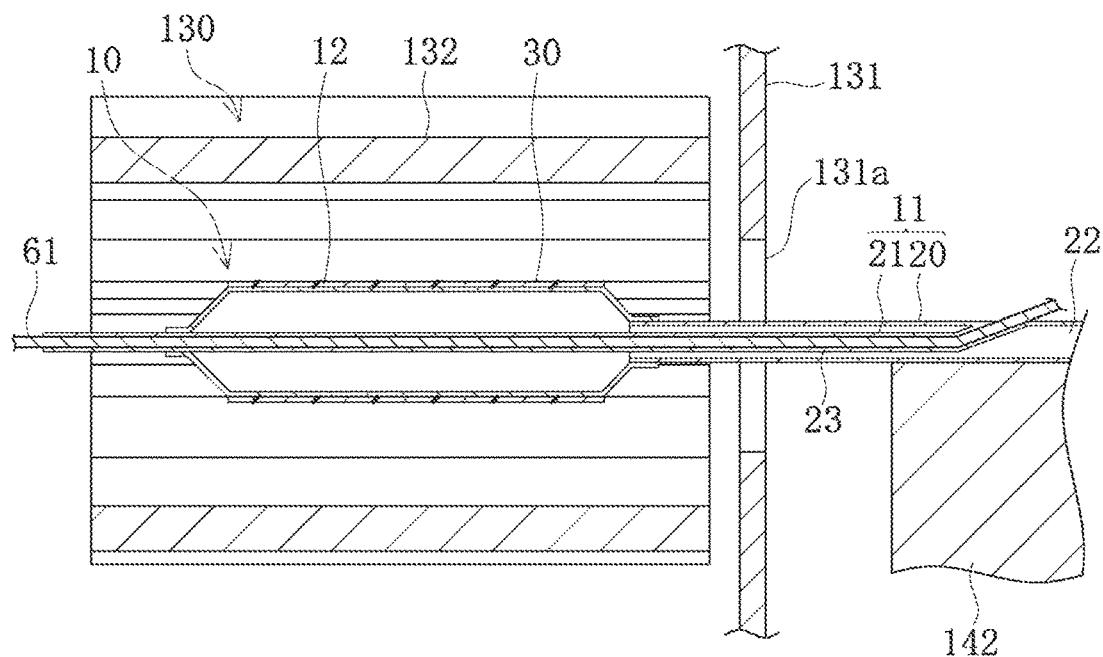
FIG. 18 is a sectional view of the balloon catheter disposed in the folding section.

By being formed with the wing portions 40 projecting, as depicted in FIGS. 17 and 6B, the balloon 12 is formed with: wing outer portions 40b pressed by the second shape forming portions 122c and constituting surfaces facing the outer circumferential side of the wing portions 40; wing inner portions 40a pressed by the tip portions of the blades 122 and constituting surfaces facing the circumferential surface portions 41 of the wing portions 40; and the circumferential surface portions 41 pressed by the first shape forming portions 122b and being along the circumferential surface of the inner tube 21.

In the process of pleating, pressing by the blades 122 is conducted while deflating the balloon 12 for forming the wing portions 40, and, therefore, strong pressing forces by the blades 122 are not needed. Therefore, even when the balloon 12 is pressed by the blades 122, the structure of the crystals formed on the surface of the balloon 12 is little changed. In other words, the elongate bodies 33 formed on the surface of the balloon 12 maintain the erected state throughout the step of pleating. Note that in the process of pleating, a step of excessively inflating the balloon 12 and then deflating the balloon 12 a little (i.e., partially deflating) or a step of inflating the balloon 12 to such an extent as not to cause excessive inflation and then deflecting the balloon 12 a little may be provided.

After the balloon 12 is formed with the wing portions 40, the blades 122 are moved rotationally in the manner of returning into their original positions, and the balloon 12 is withdrawn out of the pleating section 120. Note that since the internal volume of the balloon 12 is reduced in the process of pleating, it is preferable to regulate the three-way cock according to the volume reduction, to discharge the inflation fluid to the outside, thereby deflating the balloon 12. By this, an excessive force can be restrained from acting on the balloon 12.

Next, the holding base section 142 is moved on the upper surface of the base section 141 to be spaced from the pleating section 120, and the balloon catheter 10 is withdrawn out of the pleating section 120. Subsequently, the orientation of the support base 140 is changed, and the support base 140 is positioned at a position for facing the front surface plate 131 of the folding section 130. Thereafter, the holding base section 142 is moved on the upper surface of the base section 141, whereby the balloon catheter 10 is inserted into the folding section 130 through the insertion hole 131a, as depicted in FIG. 16. The blades 132 in the folding section 130 have already been heated to approximately 50 degrees to 60 degrees.

Figure 19:
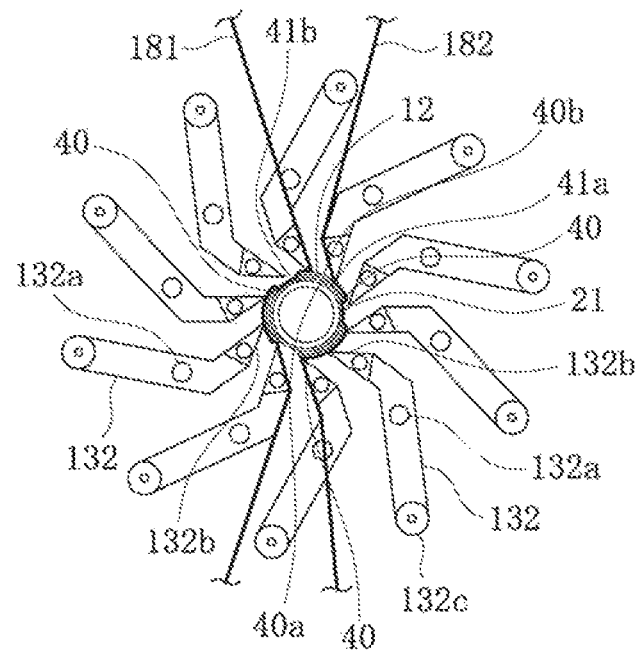
FIG. 19 is a front view depicting the blades in the folding section in a state in which the wing portions of the balloon are folded by rotationally moving the blades.

After the balloon 12 formed with the wing portions 40 is inserted into the folding section 130, the drive source 134 is operated to rotate the rotary member 133, as depicted in FIG. 19, the blades 132 are moved rotationally on the rotary member 133, and the tip portions 132b of the blades 132 approach one another, so that a central region among the blades 132 is narrowed. Attendant on this, the balloon 12 inserted in the central region among the blades 132 is put into a state in which the wing portions 40 are laid flat in the circumferential direction by the tip portions 132b of the blades 132. Since the blades 132 have preliminarily been heated before insertion of the balloon 12 and the balloon 12 is heated by the blades 132, the wing portions 40 laid flat in the circumferential direction by the blades 132 can maintain their shapes. In this instance, those surfaces of each blade 132 which make contact with the balloon 12 are covered by the first film 181 and the second film 182, so that the balloon 12 does not make direct contact with the surfaces of the blades 132.

Figure 20A:
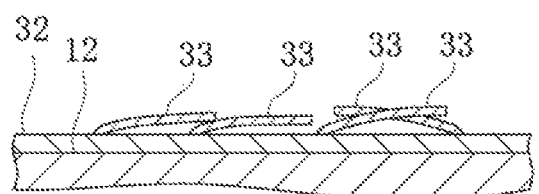
FIGS. 20A and 20B are schematic sectional views representing a process in which the elongate bodies are changed from an independent state into a non-independent state upon folding.
Figure 20B:
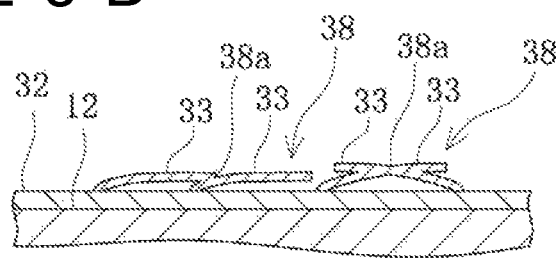

When the wing portions 40 of the balloon 12 are folded, the wing inner portions 40a of the wing portions 40 and the facing surface portions 41a of the circumferential surface portions 41 are laid on each other to make contact with each other, and, thus, portions of the surface of the balloon 12 face each other and overlap with each other, as depicted in FIGS. 19 and 6C. In addition, the wing outer portions 40b of the wing portions 40 and the outer circumference constituting surface portions 41b of the circumferential surface portions 41 are exposed to the outer circumferential side. The wing outer portions 40b and the outer circumference constituting surface portions 41b exposed to the outer circumferential side in the folded state receive pressing forces in the manner of rubbing in the circumferential direction from the first film 181 and the second film 182 both pressed by the blades 132, thereby being heated further. With the pressing forces exerted on the balloon 12 by the blades 132, the pressing time and the heating temperature being set appropriately, the elongate bodies 33 of the drug crystals provided on the wing outer portions 40b and the outer circumference constituting surface portions 41b are changed from the erected state into the state in which the plurality of elongated bodies 33 are tilted in the manner of overlapping with each other, as depicted in FIG. 20A. Further, due to the heat attendant on pressing, the overlapping elongate bodies 33 are heat fused to one another and united with one another to form the crystal conjugates 38, as depicted in FIG. 20B.

Since the wing inner portions 40a and the facing surface portions 41a which face each other and overlap with each other are not exposed to the exterior, the pressing forces from the blades 132 act thereon on the wing inner portions 40a and the facing surface portions 41a which face each other and overlap with each other indirectly. In addition, the wing inner portions 40a and the facing surface portions 41a are not in perfectly close contact with each other. For this reason, the pressing forces exerted on the elongate bodies 33 provided in these regions can be controlled to such an extent that the elongate bodies 33 can maintain the erected state. By this, in regard of the wing inner portions 40a and the facing surface portions 41a, the elongate bodies 33 can be maintained in the erected state even when the balloon 12 is folded. It is to be noted, however, that by increasing the pressing forces exerted by the blades 132, a condition may be established in which the crystal conjugates 38 are formed also in these regions which are located on the inner side of the wing portions 40.

After the wing portions 40 of the balloon 12 are folded, the blades 132 are moved rotationally in the manner of returning into their original positions. Next, the balloon catheter 10 is removed from the grasping unit 110, and the balloon 12 is withdrawn from the folding section 130. Subsequently, the holding of the catheter shaft 11 by the holding section 143 is released, the balloon 12 is covered by the tubular protective sheath 15 (see FIG. 1), and the folding of the balloon 12 of the balloon catheter 10 is completed. The protective sheath 15 is a member for restraining the drug from falling off (i.e., being removed from) the balloon 12, and the protective sheath 15 is removed before the balloon catheter 10 is put to use.

By these steps, the balloon 12 is folded. In addition, by the pressing forces at the time of folding, the elongate bodies 33 on the surface of the balloon 12 can be changed from the erected state into the tilted state. Further, by heating of the elongate bodies 33, the elongate bodies 33 can be united together to form the crystal conjugates 38.

Now, a manufacturing method according to a second mode for folding the balloon 12 while forming the crystal conjugates 38 on the surface will be described below. In the manufacturing method of the second mode, also, the configurations of the balloon coating apparatus 50 and the balloon folding apparatus 100 are the same as above, and descriptions of them will be omitted.

In the manufacturing method of the present mode, at the time of forming the crystals of the water-insoluble drug on the surface of the balloon 12 by use of the balloon coating apparatus 50, not the elongate bodies 33 in the independent state but the elongate bodies 33 in the non-independent state, or the crystal conjugates 38, are formed. By controlling the positional relation of the dispensing tube 94 to the balloon 12, the moving speed of the dispensing tube 94, the temperature condition at the time of volatilizing the organic solvent contained in the coating solution applied to the surface of the balloon 12, and the like, the crystal conjugates 38 composed of the elongate bodies 33 in the non-independent state can be formed by the balloon coating apparatus 50. In this instance, the elongate bodies 33 constituting the crystal conjugates 38 are in the erected state on the surface of the balloon 12.

Subsequently, the elongate bodies 33 in the erected state are tilted, in the process of folding the balloon 12 by the balloon folding apparatus 100. Specifically, first, the balloon 12 is formed with the wing portions 40 in the pleating section 120. Next, the wing portions 40 of the balloon 12 are folded in the folding section 130, during when the crystal conjugates 38 are tilted, by pressing and heating of the surface of the balloon 12 by the blades 132. As a result of this, the elongate bodies 33 constituting the crystal conjugates 38 are put into the tilted state relative to the surface of the balloon 12.

In this way, the balloon 12 having the crystal conjugates 38 in the tilted state can be formed, also by preliminarily forming the crystal conjugates 38 on the surface of the balloon 12 by the balloon coating apparatus 50, and tilting the crystal conjugates 38 by the balloon folding apparatus 100.

A method of using the balloon catheter 10 according to the present embodiment will be described below, taking as an example a case of treating a stenosed part in a blood vessel.

First, by a known method such as a Seldinger method, the operator percutaneously punctures a blood vessel and places an introducer (not depicted) indwelling. Next, the protective sheath 15 of the balloon catheter 10 is removed, priming is performed, and thereafter a guide wire 200 (see FIG. 21) is inserted into the guide wire lumen 23. In this state, the guide wire 200 and the balloon catheter 10 are inserted into the blood vessel through the inside of the introducer. Subsequently, the balloon catheter 10 is moved forward, with the guide wire 200 preceding, and the balloon 12 is delivered to a stenosed part 300. Note that a guiding catheter may be used for delivering the balloon catheter 10 to the stenosed part 300. At the time of inserting the balloon catheter 10, the balloon 12 in the folded state makes frictional contact with the inner wall surface of the blood vessel; however, since the crystal conjugates 38 composed of the elongate bodies 33 in the tilted state are provided on the surfaces exposed to the outer circumferential side, the crystal conjugates 38 are restrained from being caught on the inner wall surface of the blood vessel, and the drug is restrained from falling off (i.e., being removed from the balloon 12).

Figure 21:
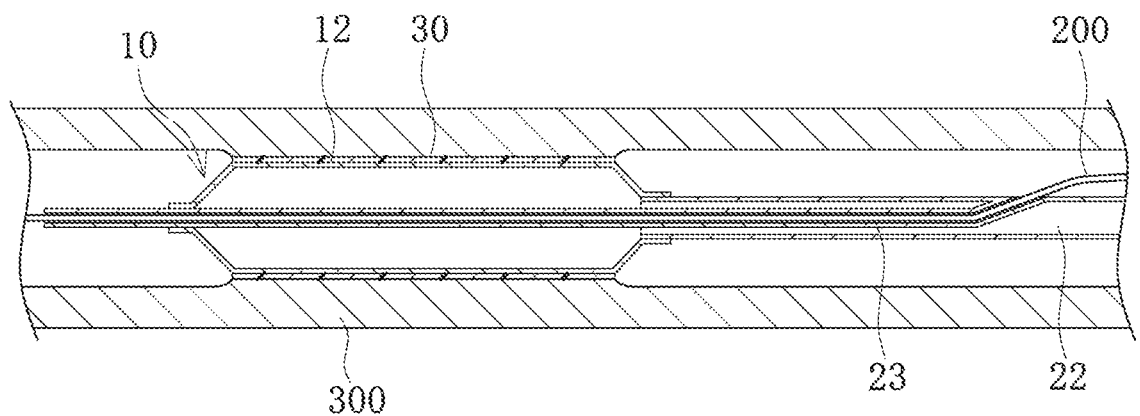
FIG. 21 is a sectional view depicting a state in which a stenosed part of a blood vessel is pushed wide open by the balloon catheter according to the present embodiment.

After the balloon 12 is disposed at the stenosed part 300, a predetermined quantity of an inflation fluid is fed from the proximal opening portion 13a of the hub 13 into the balloon 12 through the inflation lumen 22 by use of an indeflator or a syringe or the like. By this, the folded balloon 12 is inflated, and the stenosed part 300 is pushed wide open (widened) by the balloon 12, as depicted in FIG. 21. In this instance, the coating layer 30 containing the drug crystals provided on the surface of the balloon 12 makes contact with the stenosed part 300. In this process, the crystal conjugates 38 on the surface of the balloon 12 are separated to take the form of the elongate bodies 33 in the independent state, as aforementioned. When the balloon 12 is inflated and the coating layer 30 is thereby pressed against the living body tissue, the base layer 32 which is the low-molecular compound included in the coating layer 30 is dissolved gradually or rapidly, and, during when the dissolution proceeds, the drug is delivered to the living body. The elongate bodies 33 reduced in size through separation of the crystal conjugates 38 have good transferability to the living body tissue, so that the drug can be effectively transferred to the stenosed part 300. Therefore, restenosis at the stenosed part 300 is restrained effectively.

Thereafter, the inflation fluid is discharged by drawing the inflation fluid via the proximal opening portion 13a of the hub 13, whereby the balloon 12 is deflated and put into a folded state. Thereafter, the guide wire 200 and the balloon catheter 10 are drawn out of (i.e., withdrawn from) the blood vessel through the introducer, to complete the procedure.

As has been described above, the balloon catheter 10 according to the present embodiment is a balloon catheter 10 having the balloon 12 at a distal portion of the catheter shaft 11 and provided on the surface of the balloon 12 with the elongate bodies 33 which are crystals of a water-insoluble drug extending in a longitudinal direction, and the surface of the balloon 12 is provided with the crystal conjugates 38 formed of the plurality of elongate bodies 33 jointed to one another while being in a tilted state. As a result of this, at the time of inserting the balloon 12 into a body lumen, separation of the elongate bodies 33 from the surface of the balloon 12 can be restrained. In addition, when the balloon 12 is inflated at a lesion affected area, the crystal conjugates 38 are separated to be the elongate bodies 33 which are in the independent state, and, therefore, transferability of the drug to the living body tissue can be improved.

Where the elongate bodies 33 in the tilted state which form the crystal conjugates 38 are so disposed as to form angles of not more than 30 degrees relative to the surface of the balloon 12, it can be relatively ensured that the elongate bodies 33 are hardly separated from the surface of the balloon 12 at the time of inserting the balloon 12 into the body lumen.

The crystal conjugate 38 is composed of a plurality of elongate bodies 33 which overlap with each other at a position in the longitudinal direction and are joined to and united with one another. Therefore, the shapes of the elongate bodies 33 are left as they are in the crystal conjugates 38, so that the crystal conjugates 38 are easily separated, upon inflation of the balloon 12, to take the form of the elongate bodies 33 after the separation, whereby the drug can be effectively transferred to the living body tissue.

The crystal conjugates 38 are formed with cracks 38b in the crystal conjugates 38, which crack upon inflation of the balloon 12. Therefore, when the surface of the balloon 12 is pressed against the living body tissue, the crystal conjugates 38 are separated to assume the form of the independent elongate bodies 33, so that the drug can be easily transferred to the living body tissue.

Where the water-insoluble drug is rapamycin, paclitaxel, docetaxel, or everolimus, restenosis at a stenosed part in a body lumen can be restrained favorably.

In addition, a method of manufacturing a balloon catheter 10 according to the present embodiment is a method of manufacturing a balloon catheter 10 provided on a surface of a balloon 12 with elongate bodies 33 which are crystals of a water-insoluble drug extending in a longitudinal direction, the method including: a step of forming the elongate bodies 33 having mutually independent long axes on the surface of the balloon 12; a step of forming the balloon 12 with wing portions 40 projecting in radial directions; and a step of laying the wing portions 40, formed in the balloon 12, flat along a circumferential direction. In either the step of forming the balloon 12 with the wing portions 40 or the step of laying flat the wing portions 40 of the balloon 12, the mutually independent elongate bodies 33 on the surface of the balloon 12 are united with the adjacent elongate bodies 33 while tilting them by a force and heat applied for deforming the balloon 12, thereby to form crystal conjugates 38 in which the plurality of the elongate bodies 33 overlap with each other at a position in the longitudinal direction and are united with one another. By this, in either the step of forming the balloon 12 with the wing portions 40 or the step of laying flat the wing portions 40 of the balloon 12, the crystal conjugates 38 in the state in which the elongate bodies 33 are tilted can be formed on the surface of the balloon 12, by utilization of the force and heat applied for deforming the balloon 12.

In addition, a method of manufacturing a balloon catheter 10 according to the present embodiment is a method of manufacturing a balloon catheter 10 provided on a surface of a balloon 12 with elongate bodies 33 which are crystals of a water-insoluble drug extending in a longitudinal direction, the method including: a step of forming on the surface of the balloon 12 crystal conjugates 38 in which the plurality of elongate bodies 33 overlap with each other at a position in the longitudinal direction and are united with one another; a step of forming the balloon 12 with wing portions 40 projecting in radial directions; and a step of laying the wing portions 40, formed in the balloon 12, flat along a circumferential direction. In either the step of forming the balloon 12 with the wing portions 40 or the step of laying flat the wing portions 40 of the balloon 12, the crystal conjugates 38 are tilted relative to the surface of the balloon 12 by a force and heat applied for deforming the balloon 12. By this, in either the step of forming the balloon 12 with the wing portions 40 or the step of laying flat the wing portions 40 of the balloon 12, the elongate bodies 33 that constitute the crystal conjugates 38 having been preliminarily formed on the surface of the balloon 12 can be tilted, by utilization of the force and heat applied for deforming the balloon 12.

In addition, a treatment method according to the present embodiment is a treatment method of delivering a drug to a lesion affected area in a body lumen by use of the balloon catheter 10, the treatment method including: a step of inserting the balloon 12 into the body lumen to deliver the balloon 12 to the lesion affected area; a step of inflating the balloon 12 to press the elongate bodies 33 against living body tissue; and a step of deflating the balloon 12 and withdrawing the balloon 12 out of the body lumen. By this, at the time of moving the balloon 12 in the folded state within a blood vessel, it is possible, owing to the presence of the crystal conjugates 38, to restrain the drug from being lost (i.e., removed from the balloon) during insertion of the balloon 12, and to effectively deliver the drug to the target position. Upon inflation of the balloon 12 at the lesion affected area, the crystal conjugates 38 come to take the form of the elongate bodies 33, whereby the drug can be effectively transferred to the lesion affected area.

At the time of inflating the balloon 12, cracks are formed in the crystal conjugates 38 on the balloon 12. Therefore, when the surface of the balloon 12 is pressed against living body tissue, the crystal conjugates 38 are separated to assume the form of the independent elongate bodies 33, whereby the drug can be relatively easily transferred to the living body tissue.

Note that the present disclosure is not limited only to the aforementioned embodiments, and various modifications can be made by those skilled in the art within the technical thought of the disclosure. For example, while the balloon catheter 10 according to the above embodiments is of the rapid exchange type, the balloon catheter may be of the over-the-wire type.

In addition, while the elongate bodies 33 formed on the surface of the balloon 12 are converted into the crystal conjugates 38 in the process of folding of the balloon 12 in the present embodiment, the conversion from the elongate bodies 33 into the crystal conjugates 38 may be effected by pressing and heating by the blades 122 in the process of pleating (see FIG. 17).

Figure 22:
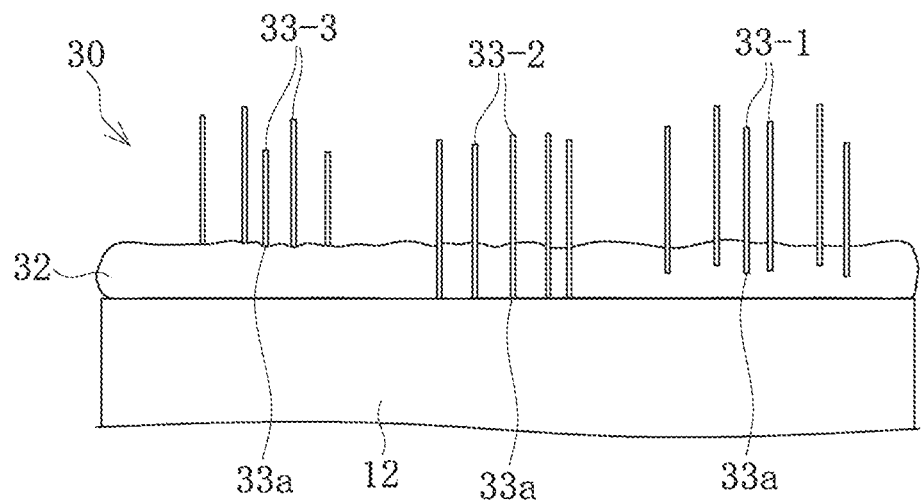
FIG. 22 is a schematic view of elongate bodies and a base layer in a case where the base layer is in a film-shaped amorphous state.
Figure 23:
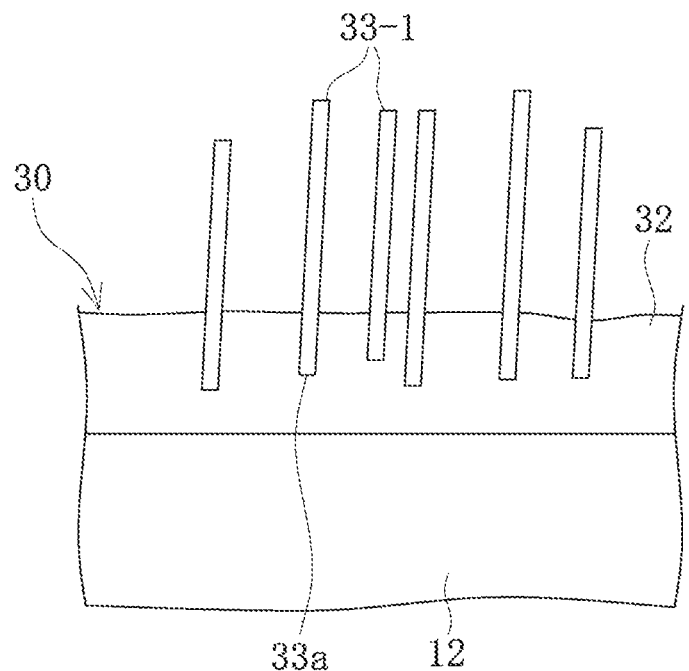
FIG. 23 is a schematic view of first elongate bodies and the base layer, on an outer surface of a balloon.
Figure 24:
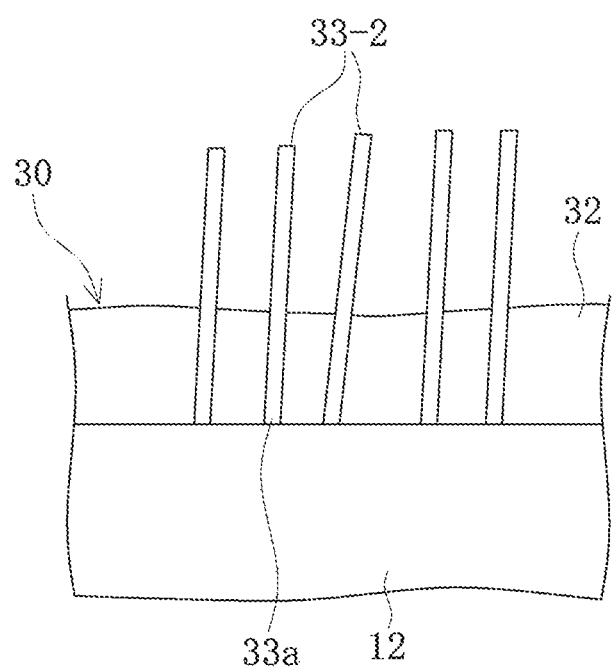
FIG. 24 is a schematic view of second elongate bodies and the base layer, on the outer surface of the balloon.
Figure 25:
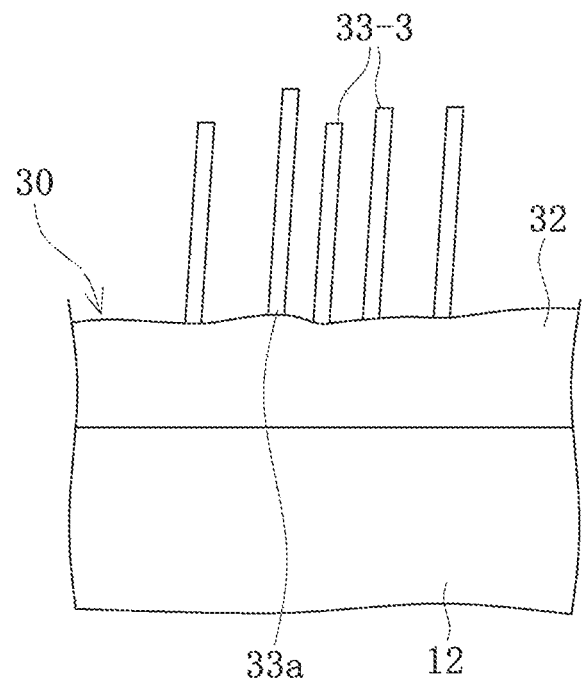
FIG. 25 is a schematic view of third elongate bodies and the base layer, on the outer surface of the balloon.

As aforementioned, the base layer 32 is present as an amorphous phase, crystal particles, or a mixture of the amorphous phase and crystal particles. While the base layer 32 in FIG. 4 is in a state of crystal particles and/or a particulate amorphous phase, the base layer 32 may be in a film-shaped amorphous state, as depicted in FIG. 22. As depicted in FIG. 23, first elongate bodies 33-1 extend from the inside of the base layer 32 to the outside of the base layer 32. As depicted in FIG. 24, second elongate bodies 33-2 extend from the outer surface of the balloon 12 to the outside of the base layer 32 by penetrating the base layer 32. As depicted in FIG. 25, third elongate bodies 33-3 extend from the outer surface of the base layer 32 toward the outside of the surface.

Figure 26:
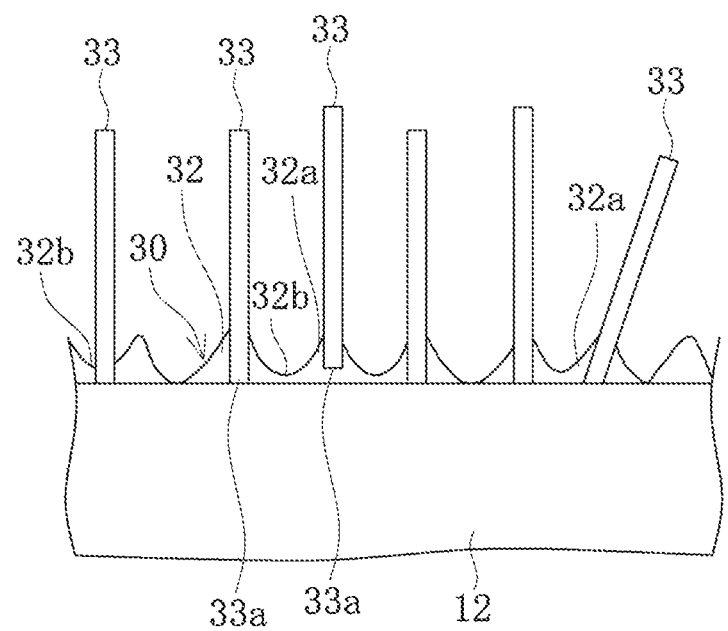
FIG. 26 is a schematic view of the elongate bodies and the base layer, on the outer surface of the balloon.

In addition, as depicted in FIG. 26, the base layer 32 which is an additive layer may have projections and recesses (i.e., ruggedness). The height of the projections can be, for example, 0.1 μm to 5 μm. The elongate bodies 33 which are crystals are projecting from projecting portions 32a that constitute the projections of the base layer 32. In other words, the elongate bodies 33 which are crystals are supported by the projecting portions 32a of the base layer 32. Note that the base layer 32 may have the projecting portions 32a from which the elongate bodies 33 are not projecting.

The elongate bodies 33 which are crystals may project from recessed portions 32b that constitute the recesses of the base layer 32. The base layer 32 may have both the projecting portions 32a which support the elongate bodies 33 and the projecting portions 32a which do not support the elongate bodies 33. The base layer 32 may have both the recessed portions 32b which support the elongate bodies 33 and the recessed portions 32b which do not support the elongate bodies 33. In addition, the base layer 32 may have both the projecting portions 32a which support the elongate bodies 33 and the recessed portions 32b which support the elongate bodies 33. The elongate bodies 33 may project obliquely from the base layer 32 such as to be tilted relative to the outer surface of the balloon 12. The base layer 32 may have both the elongate bodies 33 which are substantially perpendicular to the outer surface of the balloon 12 and the elongate bodies 33 which are tilted relative to the outer surface of the balloon 12. The base portions 33a of the elongate bodies 33 may be in direct contact with the outer surface of the balloon 12. Alternatively, the base portions 33a of the elongate bodies 33 may be located in the inside of the base layer 32, without making contact with the outer surface of the balloon 12. The base layer 32 may have both the elongate bodies 33 which are in direct contact with the outer surface of the balloon 12 and the elongate bodies 33 which are not in contact with the outer surface of the balloon 12.

Figure 27:
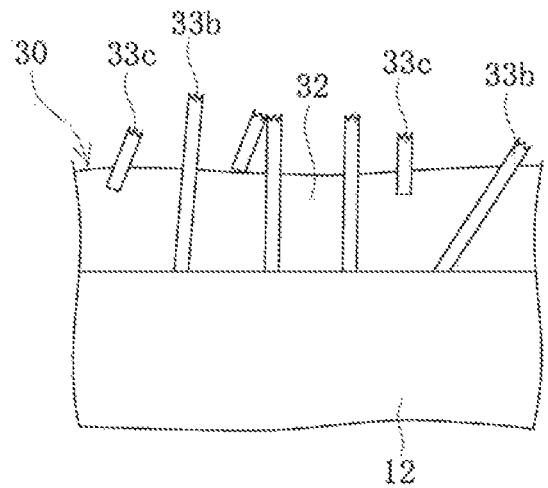
FIG. 27 is a schematic view of fixed-side elongate bodies, separate-side elongate bodies and the base layer, on the outer surface of the balloon.

In addition, as depicted in FIG. 27, the crystals may include fixed-side elongate bodies 33b (balloon base material contact crystal particles) originally projecting from the base layer 32, and separate-side elongate bodies 33c (balloon base material non-contact crystal particles) separated from the fixed-side elongate bodies 33b. The amount of the fixed-side elongate bodies 33b is larger than that of the separate-side elongate bodies 33c. The separate-side elongate bodies 33c are formed by breaking of elongate crystals and separation from the fixed-side elongate bodies 33b when the balloon 12 is folded in the manner of winding around the inner tube 21. Of the fixed-side elongate bodies 33b and the separate-side elongate bodies 33c, at least part is tilted attendant on the folding of the balloon 12, and they are united with the adjacent elongate bodies by heating, to form the crystal conjugates 38. At least part of a distal portion, a proximal portion, and a portion between the distal portion and the proximal portion, of the separate-side elongate body 33c, is in contact with the base layer 32. Part of the separate-side elongate body 33c may be embedded in the base layer 32. The presence of the base layer 32 helps ensure that the fixed-side elongate bodies 33b and the separate-side elongate bodies 33c are not liable to fall off the balloon 12 during carrying, because of their interactions with the base layer 32. The fixed-side elongate bodies 33b and the separate-side elongate bodies 33c become liable to be released through dissolution of the base layer 32 upon contact with water (blood) when the balloon 12 is inflated. The fixed-side elongate bodies 33b and the separate-side elongate bodies 33c differing in morphological form are different in releasing property, which is preferable from the viewpoint of their action on the living body. The fixed-side elongate bodies 33b may be formed through breaking of crystals, or may be formed without breaking of crystals. The base layer 32 may include both the fixed-side elongate bodies 33b formed through breaking of crystals, and the fixed-side elongate bodies 33b formed without breaking of crystals.

The length of the crystals fixed to the base layer 32, before breaking of the crystals fixed to the base layer 32, is 5 μm to 20 μm, for example. The length of the broken crystals is, for example, 3 µm to 20 µm. The length of the fixed-side elongate bodies 33*b* formed through breaking is, for example, 5 µm to 20 µm. The length of the separate-side elongate bodies 33*c* is, for example, 3 to 10 µm.

Figure 28A:
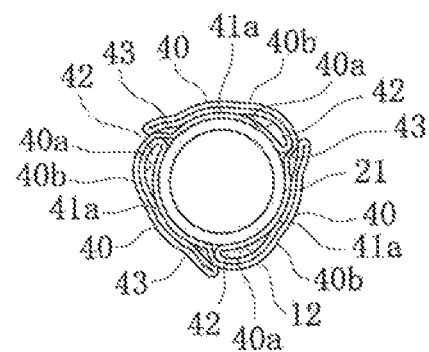
FIGS. 28A and 28B are sectional views of balloons in a folded state that have wing portions in different forms.
Figure 28B:
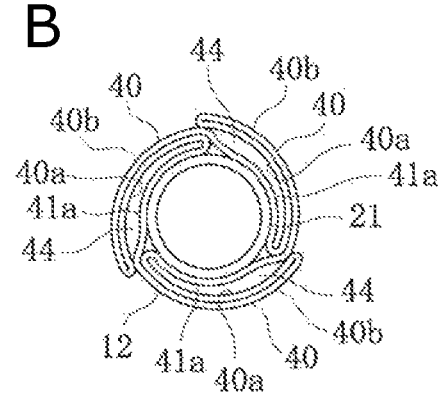

In addition, in the present embodiment, tip ends of the wing portions 40 of the balloon 12 folded do not reach the adjacent wing portions 40, but the tip ends may reach the adjacent wing portions 40 as in two examples depicted in FIGS. 28A and 28B. In the example of FIG. 28A, a root-side space portion 42 is formed between the root side of the wing portion 40 and the circumferential surface portion 41, and a tip-side space portion 43 is formed between the tip side of the wing portion 40 and the circumferential surface portion 41. In the example of FIG. 28B, a space portion 44 is formed between the wing portion 40 and the circumferential surface portion 41, throughout the region ranging from the root side of the wing portion 40 to the adjacent wing portion 40.

The detailed description above describes a balloon catheter having a balloon coated on a surface of the balloon with a drug, a method of manufacturing the balloon catheter, and a treatment method. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A balloon catheter, the balloon catheter comprising:
   a balloon at a distal portion of a catheter shaft, the balloon including a plurality of elongated bodies, the plurality of elongated bodies being crystals of a water-insoluble drug, each of the plurality of elongated bodies possessing an independent longitudinal axis and extending in a direction away from an outer surface of the balloon;
   a crystal conjugate formed of the plurality of elongated bodies that are joined by heat fusion or press bonding to one another while being in a tilted state on the outer surface of the balloon; and
   wherein the crystal conjugate is cracked when the balloon is inflated.

2. The balloon catheter according to claim 1, wherein the plurality of elongated bodies in the tilted state that form the crystal conjugate form angles of not more than 30 degrees relative to the outer surface of the balloon.

3. The balloon catheter according to claim 1, wherein the crystal conjugate is formed by the heat fusion or press bonding in which the plurality of the elongated bodies overlap with each other and are joined to and united with one another.

4. The balloon catheter according to claim 1, wherein the water-insoluble drug is rapamycin, paclitaxel, docetaxel, or everolimus.

5. The balloon catheter according to claim 1, wherein the balloon in a deflated state has a plurality of wing portions in a circumferential direction of the balloon and a circumferential surface portion along a circumferential direction of the catheter shaft, the wing portions being folded along the circumferential direction of the balloon.

6. The balloon catheter according to claim 1, wherein the plurality of elongated bodies each include a base end, a tip end and a side surface, the base end of each of the plurality of elongated bodies being located on the outer surface of the balloon.

7. The balloon catheter according to claim 6, wherein the plurality of elongated bodies include solid elongated bodies and hollow elongated bodies, the hollow elongated bodies including at least a portion near the tip end that is hollow.

8. The balloon catheter according to claim 1, wherein the plurality of elongated bodes are substantially rectilinear in a long axis direction.

9. The balloon catheter according to claim 1, comprising:
   a base layer, the base layer being a water-insoluble drug distributed into spaces between each of the plurality of elongated bodies.

10. The balloon catheter according to claim 9, wherein the base layer comprises a plurality of crystal particles.

11. The balloon catheter according to claim 9, wherein the plurality of elongated bodies comprise:
    first elongated bodies that extend from an outer surface of the base material toward the outside of the surface;
    second elongated bodies that extend from the outer surface of the balloon to an outside of the base material by penetrating the base material; and
    third elongated bodies that extend from an inside of the base material to the outside of the base material.

12. The balloon catheter according to claim 1, wherein the plurality of elongated bodies each has a length of 5 µm to 20 µm.

13. The balloon catheter according to claim 1, wherein when the crystal conjugate is cracked, the crystal conjugate is separated into independent elongated bodies.

14. A treatment method of delivering a drug to a lesion affected area in a body lumen by use of a balloon catheter, the balloon catheter including a balloon at a distal portion of a catheter shaft, the balloon including a plurality of elongated bodies, the plurality of elongated bodies being crystals of a water-insoluble drug, each of the plurality of elongated bodies possessing an independent longitudinal axis and extending in a direction away from an outer surface of the balloon, and a crystal conjugate formed of the plurality of elongated bodies that are joined by heat fusion or press bonding to one another while being in a tilted state on the outer surface of the balloon, the treatment method comprising:
    inserting the balloon into the body lumen to deliver the balloon to the lesion affected area;
    inflating the balloon to press the plurality of elongated bodies against living body tissue; and
    cracking the crystal conjugate when the balloon is inflated.

15. The treatment method according to claim 14, further comprising:
    deflating the balloon and withdrawing the balloon out of the body lumen.

16. The treatment method according to claim 14, wherein the plurality of elongated bodies in the tilted state that form the crystal conjugate form angles of not more than 30 degrees relative to the outer surface of the balloon.

17. The treatment method according to claim 14, wherein the crystal conjugate is formed by the heat fusion or press bonding in which the plurality of elongated bodies overlap with each other direction and are joined to and united with one another.

18. The treatment method according to claim 14, wherein the water-insoluble drug is rapamycin, paclitaxel, docetaxel, or everolimus.

* * * * *